Figure 1C:
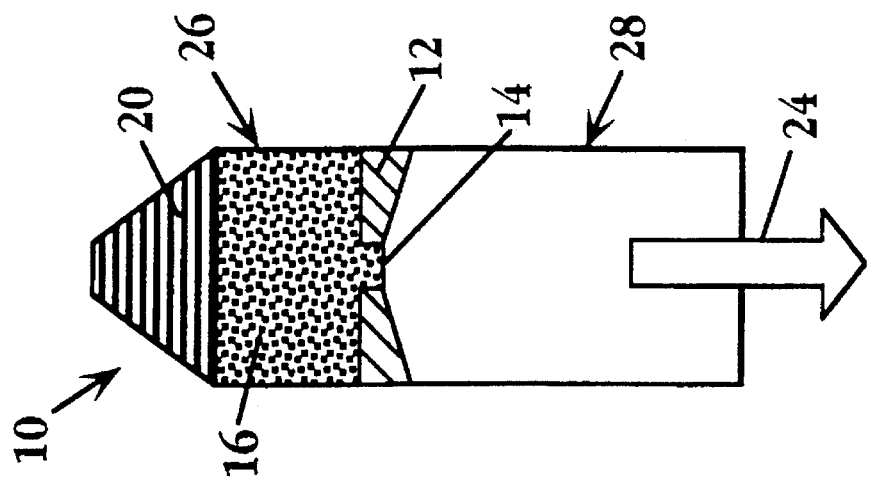

United States Patent [19]

Van Vlasselaer

[11] Patent Number: 5,474,687
[45] Date of Patent: Dec. 12, 1995

[54] METHODS FOR ENRICHING CD34+ HUMAN HEMATOPOIETIC PROGENITOR CELLS

[75] Inventor: Peter Van Vlasselaer, Sunnyvale, Calif.

[73] Assignee: Activated Cell Therapy, Inc., Mountain View, Calif.

[21] Appl. No.: 299,469

[22] Filed: Aug. 31, 1994

[51] Int. Cl.$^6$ .................................................. B01D 33/15
[52] U.S. Cl. ........................... 210/782; 604/49; 604/187; 604/191; 494/16; 422/102; 422/72; 435/2
[58] Field of Search .................................. 494/16, 85, 44, 494/43, 45; 435/2, 7, 21; 422/102, 72, 69; 604/181, 187, 191, 38, 49; 210/781, 782

[56] References Cited

U.S. PATENT DOCUMENTS

| | | |
|---|---|---|
| 3,441,205 | 4/1969 | Young, Jr. . |
| 3,513,976 | 5/1970 | James . |
| 3,706,305 | 12/1972 | Berger et al. . |
| 3,706,306 | 12/1972 | Berger et al. . |
| 3,750,645 | 8/1973 | Bennett et al. . |
| 3,849,072 | 11/1974 | Ayres . |
| 3,937,211 | 2/1976 | Merten . |
| 3,957,654 | 5/1976 | Ayres . |
| 3,965,889 | 6/1976 | Sachs . |
| 3,985,122 | 10/1976 | Topham . |
| 4,001,122 | 1/1977 | Griffin . |
| 4,020,831 | 5/1977 | Adler . |
| 4,022,576 | 5/1977 | Parker . |
| 4,040,959 | 8/1977 | Berman et al. . |
| 4,055,501 | 10/1977 | Cornell . |
| 4,066,414 | 1/1978 | Selby . |
| 4,112,924 | 9/1978 | Ferrara et al. . |
| 4,134,512 | 1/1979 | Nugent . |
| 4,147,628 | 4/1979 | Bennett et al. . |
| 4,152,270 | 5/1979 | Cornell . |
| 4,181,700 | 1/1980 | Chervenka et al. . |
| 4,213,456 | 7/1980 | Böttger . |
| 4,256,120 | 3/1981 | Finley . |

(List continued on next page.)

FOREIGN PATENT DOCUMENTS

0595641A2  10/1993  European Pat. Off. .
WO93/08268  4/1993  WIPO .

OTHER PUBLICATIONS

Dicke et al., 1968, "The Selective Elimination of Immunologically Competent Cells From Bone Marrow and Lymphatic Cell Mixtures," *Transplantation* 6(4):562–570.

Dicke et al., 1970, "Avoidance of Acute Secondary Disease by Purification of Hemopoietic Stem Cells with Density Gradient Centrifugation," *Exp. Hematol* 20:126–130.

Dicke et al., 1971, "Allogeneic Bone Marrow Transplantation After Elimination of Immunocompetent Cells by Means of Density Gradient Centrifugation," *Transplantation Proceedings* 3(1):666–668.

Dicke et al., 1973, "The Use of Stem Cell Concentrates As Bone Marrow Grafts in Man," *Transplantation Proceedings* 5(1):909–912.

(List continued on next page.)

*Primary Examiner*—C. Fred Rosenbaum
*Assistant Examiner*—Perry E. Van Over

[57] ABSTRACT

The present invention relates to methods of enriching hematopoietic progenitor cells from body fluids. In particular, it relates to the use of a cell-trap centrifugation tube containing a gradient solution adjusted to a specific density to enrich for CD34+ cells from apheresed blood. The tube allows the desired cell population to be collected by decantation after centrifugation to minimize cell loss and maximize efficiency. In addition, the method can be further simplified by density-adjusted cell sorting which uses cell type-specific binding agents such as antibodies and lectins linked to carrier particles to impart a different density to undesired cell populations allowing the progenitor cells to be separated during centrifugation in a more convenient manner. The rapid progenitor cell enrichment method described herein has a wide range of applications, including but not limited to, donor cell preparation for bone marrow transplantation without the use of invasive procedures such as bone marrow aspiration.

32 Claims, 11 Drawing Sheets

U.S. PATENT DOCUMENTS

| | | |
|---|---|---|
| 4,378,812 | 4/1983 | Sarstedt . |
| 4,443,345 | 4/1984 | Wells . |
| 4,459,997 | 7/1984 | Sarstedt . |
| 4,511,349 | 4/1985 | Nielsen et al. . |
| 4,562,844 | 1/1986 | Carpenter et al. . |
| 4,569,764 | 2/1986 | Satchell . |
| 4,610,846 | 9/1986 | Martin . |
| 4,707,276 | 10/1987 | Dodge et al. . |
| 4,824,560 | 4/1989 | Alspector . |
| 4,828,716 | 5/1989 | McEwen et al. . |
| 4,844,818 | 7/1989 | Smith . |
| 4,886,071 | 12/1989 | Mehl et al. . |
| 4,917,801 | 4/1990 | Luderer et al. . |
| 4,927,749 | 5/1990 | Dorn . |
| 4,927,750 | 5/1990 | Dorn . |
| 4,954,264 | 9/1990 | Smith . |
| 4,957,638 | 9/1990 | Smith . |
| 5,030,341 | 7/1991 | McEwen et al. . |
| 5,039,401 | 8/1991 | Columbus et al. . |
| 5,053,134 | 10/1991 | Luderer et al. . |
| 5,061,620 | 10/1991 | Tsukamoto et al. . |
| 5,132,232 | 7/1992 | Parker . |
| 5,236,604 | 8/1993 | Fiehler . |
| 5,248,480 | 9/1993 | Greenfield et al. . |
| 5,269,927 | 12/1993 | Fiehler . |
| 5,271,852 | 12/1993 | Luoma, II . |
| 5,308,506 | 5/1994 | McEwen . |

OTHER PUBLICATIONS

Korbling, et al., 1977, "Procurement of Human Blood Stem Cells by Continuous-Flow Centrifugation—Further Comment," *Blood* 50(4):753–754

Olofsson et al., 1980, "Separation of Human Bone Marrow Cells in Density Gradients of Polyvinylpyrrolidone Coated Silica Gel (Percoll)," *Scand. J. Haematol.* 24:254–262.

Ellis et al., 1984, "The Use of Discontinuous Percoll Gradients to Separate Populations of Cells from Human Bone Marrow and Peripheral Blood," *J. Immunol. Methods* 66:9–16.

Lasky et al., 1985, "Size and Density Characterization of Human Committed and Multipotent Hematopoietic Progenitors" *Exp. Hematol.* 13:680–4.

Martin et al., 1986, "Purification of Haemopoietic Progenitor Cells From Patients with Chronic Granulocytic Leukaemia Using Percoll Density Gradients and Elutriation" *Brit. J. Haematol.* 63(1):187–98.

Lebkowski et al., 1992, "Rapid Isolation of Human CD34 Hematopoietic Stem Cells Purging of Human Tumor Cells" *Transplantation* 53(5):1011–1019.

Ikuta et al., 1992, "Lymphocyte Development From Stem Cells" *Ann. Rev. Immunol.* 10:759–83.-

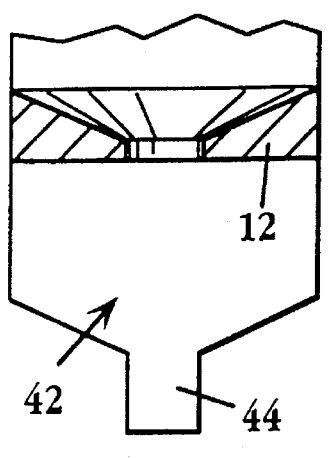 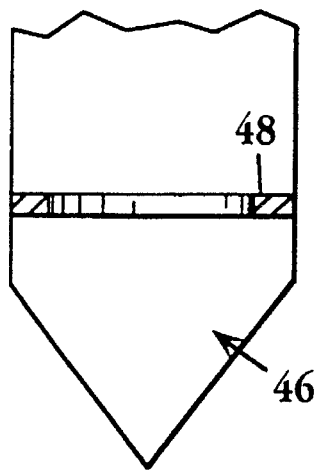 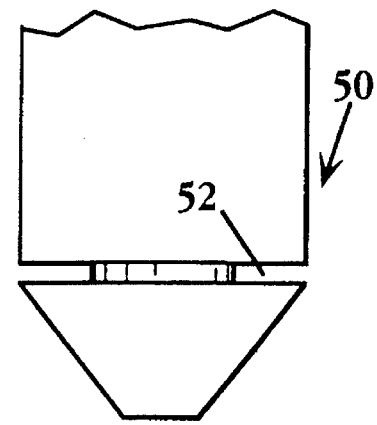
Fig.5A  Fig.5B  Fig.5C
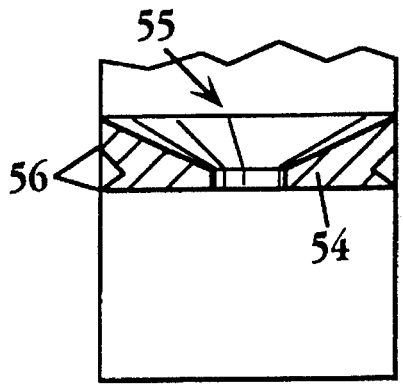 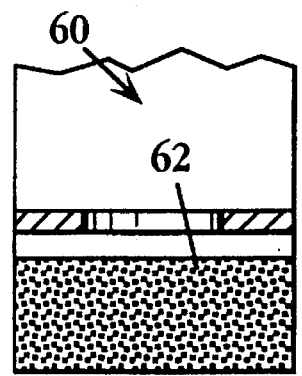 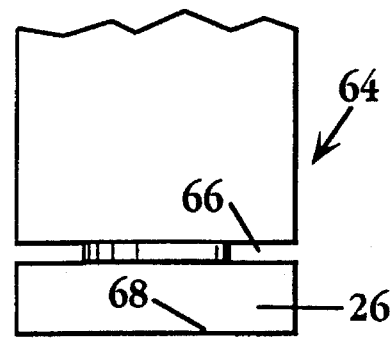
Fig.5D  Fig.5E  Fig.5F
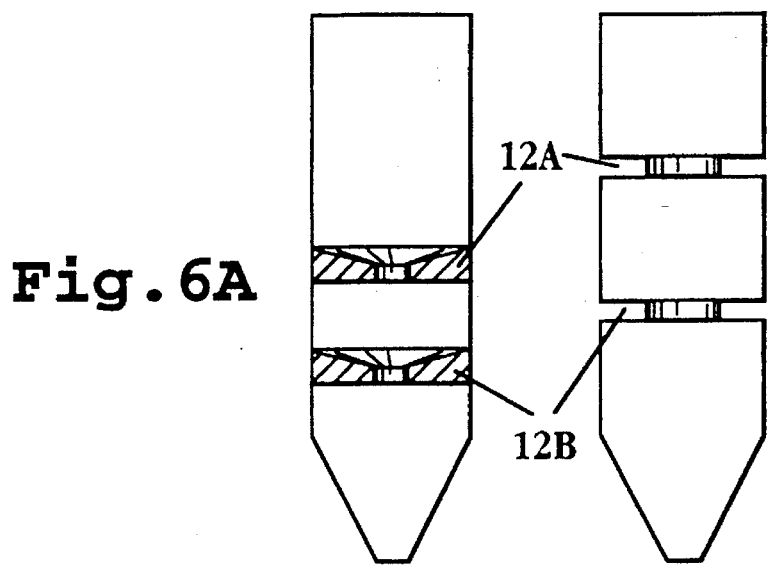
Fig.6A  Fig.6B

METHODS FOR ENRICHING CD34+ HUMAN HEMATOPOIETIC PROGENITOR CELLS

1. INTRODUCTION

The present invention relates to methods of enriching hematopoietic progenitor cells from body fluids. In particular, it relates to the use of a cell-trap centrifugation tube containing a gradient solution adjusted to a specific density to enrich for CD34+ cells from apheresed blood. The tube allows the desired cell population to be collected by decantation after centrifugation to minimize cell loss and maximize efficiency. In addition, the method can be further simplified by density-adjusted cell sorting which uses cell type-specific binding agents such as antibodies and lectins linked to carrier particles to impart a different density to undesired cell populations allowing the progenitor cells to be separated during centrifugation in a more convenient manner. The rapid progenitor cell enrichment method described herein has a wide range of applications, including but not limited to, donor cell preparation for bone marrow transplantation without the use of invasive procedures such as bone marrow aspiration.

2. BACKGROUND OF THE INVENTION

Bone marrow and peripheral blood progenitor cell transplantation are clinical procedures in which donor bone marrow or peripheral blood cells are transplanted into a recipient for the reconstitution of the recipient's lymphohematopoietic system. Prior to the transplant, the recipient's own blood system is either naturally deficient or intentionally destroyed by agents such as irradiation. In cases where the recipient is a cancer patient, ablative therapy is often used as a form of cancer treatment which also destroys the cells of the lymphohematopoietic system. The success rate of this procedure depends on a number of critical factors, which include the number of hematopoietic progenitor cells in the donor cell preparation, matching between donor and recipient at the major histocompatibility complex (MHC) which encodes products that induce graft rejection, and conditioning of the recipient prior to transplantation.

Tissue typing technology has ushered in dramatic advances in the use of allogeneic bone marrow cells as a form of therapy in patients with deficient or abnormal hematopoiesis. Conditioning of a recipient can be achieved by total body or total lymphoid irradiation. However, methods to enrich for the hematopoietic progenitor cell in a donor cell preparation are still not fully perfected. A pluripotent progenitor cell is believed to be capable of self-renewal and differentiation into blood cells of various lineages including lymphocytes, granulocytes, macrophages/monocytes, erythrocytes and megakaryocytes (Ikuta et al., 1992, Ann. Rev. Immunol. 10:759). Recent studies have shown that progenitor cells reside in the CD34+ cell population in that anti-CD34 antibody-purified CD34+ cells can repopulate all hematopoietic cell types in lethally-irradiated patients. The mechanism by which a progenitor cell commits to a specific cell lineage has not been fully elucidated. However, it is clear that such events must, in part, be influenced by a variety of growth and differentiation factors that specifically regulate hematopoiesis. Other factors which are not yet identified may also be involved (Metcalf, 1989, Nature 339:27). The commonly known hematopoietic factors include erythropoietin (EPO), granulocyte/macrophage colony stimulating factor (G/M-CSF), granulocyte colony-stimulating factor (G-CSF), macrophage colony-stimulating (M-CSF), interleukin 1–12 (IL-1 to IL-12), and progenitor cell factor (SCF).

The ability to enrich for CD34+ cells is critical to the application of bone marrow transplantation as a form of therapy for hematopoietic disorders. Neoplastic transformation, immunodeficiency, genetic abnormalities, and even viral infections can all affect blood cells of different lineages and at different stages of development. Bone marrow transplantation provides a potential means for treating all such disorders. In addition, although bone marrow transplantation may not be used as a direct form of treatment for solid tumors, it provides an important means of maintaining survival of patients following various ablative therapeutic regimens. Current conventional therapy utilizes whole bone marrow harvested from the iliac crest but this approach has certain limitations. For example, bone marrow progenitor cells are present in extremely low numbers, and bone marrow aspiration involves painful invasive procedures.

If the bone marrow cells or other progenitor cell source contain contaminating tumor cells that must be purged prior to re-infusion in an autologous setting, the large number of total cells with a low percentage of CD34+ cells makes it technically difficult to perform adequate purging of tumor cells. Thus, there remains a need for a simple method for enriching CD34+ progenitor cells from a cell mixture containing higher numbers of these cells that are amenable to efficient purging of residual tumor cells for use in subsequent transplantation.

In an effort to address these problems, investigators have focused on the use of anti-CD34 antibodies. Such procedures involve positive selection, such as the passage of white blood cells over a column containing anti-CD34 antibodies or binding of cells to magnetic bead-conjugated anti-CD34 antibodies or by panning on anti-CD34-coated plates, and collecting the bound cells. However, the affinity based methods have practical limitations in that they are not reusable and are costly.

Alternative methods for enriching hematopoietic progenitor cells have been reported which utilized various forms of density gradient centrifugation (Olofsson et al., 1980, Scan. J. Haematol. 24:254; Ellis et al., 1984, J. Immunol. Meth. 66:9; Lasky and Zanjani, 1985, Exp. Hematol. 13:680; Martin et al., 1986, Brit. J. Haematol. 63:187). However, all reported methods use agar colony assays to identify hematopoietic progenitor cells after enrichment. It is known that the progenitor assays only detect committed precursor cells which occupy less than 1% of the CD34+ population. It is therefore uncertain whether these methods can in fact enrich for the early progenitor cells or stem cells which can permanently engraft and reconstitute a lymphohematopoietic system, as they have not been tested clinically. Furthermore, there is no indication from the published reports that any of these procedures are able to obtain adequate numbers of cells for clinical use.

3. SUMMARY OF THE INVENTION

The present invention relates to methods of enriching hematopoietic progenitor cells from body fluids such as peripheral blood or bone marrow, and cell-trap centrifugation tubes with a constriction for use in rapid and high yield isolation of such cells. Reports have shown that a small number of CD34+ cells circulate in cytokine-mobilized blood. The ability to enrich such cells from the peripheral blood for use in bone marrow transplantation would circumvent conventional methods which involve invasive procedures such as aspiration from the iliac crest. However, current methods for isolating the cells from the blood mainly utilize antibodies which result may affect the function of the progenitor cells as a result of antibody binding. Also, such procedure is costly for routine clinical use.

The invention is based, in part, on Applicant's discovery that colloidal silica (PERCOLL) solution adjusted to a density of 1.0605±0.0005 gr/ml, an osmolality of 280±10 mOsm/kg $H_2O$, and pH 7.4 efficiently separates $CD34^+$ cells from the majority of blood cells when apheresed blood or bone marrow buffy coat is overlaid on the gradient solution. In addition, the method is improved by using cell-trap centrifugation tubes described herein which contain a constriction to allow the cells in the upper portion (i.e. above the constriction) to be decanted as opposed to using a pipette to collect the cells which results in increased cell loss. The efficiency of the method is further improved when it is combined with the use of cell type-specific binding agents such as antibodies conjugated to heavy carrier particles in a manner by which the antibodies bind to antigens expressed by undesired cell populations, causing them to have a higher density so that they are pelleted during centrifugation. This method is hereinafter referred to as density adjusted cell sorting. Thus, this specific embodiment of the invention provides for a rapid and high yield procedure to enrich for progenitor cells from a large blood volume. The increased number of progenitor cells in the resultant cell population enhances their use in transplantation.

An advantage of the methods of the present invention is that in a single step, it reduces the total volume of infusate by 70–90%, thereby reducing the amount of cryopreservative required. After enrichment, the final cell preparation represents between 10% to 30% of the starting cell number, but contains between 70% and 100% of the starting number of $CD34^+$ cells and colony-forming CFU's. Due to this high yield (70% to 100%) of $CD34^+$ cells, a single peripheral blood collection may yield sufficient $CD34^+$ cells to reconstitute the hematopoietic and immune system of patients undergoing ablative chemotherapy. This cell population also contains a reduced number of T cells, but a substantial number of natural killer cells and natural suppressor cells. Additionally, the procedure is rapid, convenient and cost effective. Processing of a complete sample requires no specialized instrumentation and can be performed by one person in a time frame of one hour.

4. BRIEF DESCRIPTION OF THE DRAWINGS

Figure 1B:
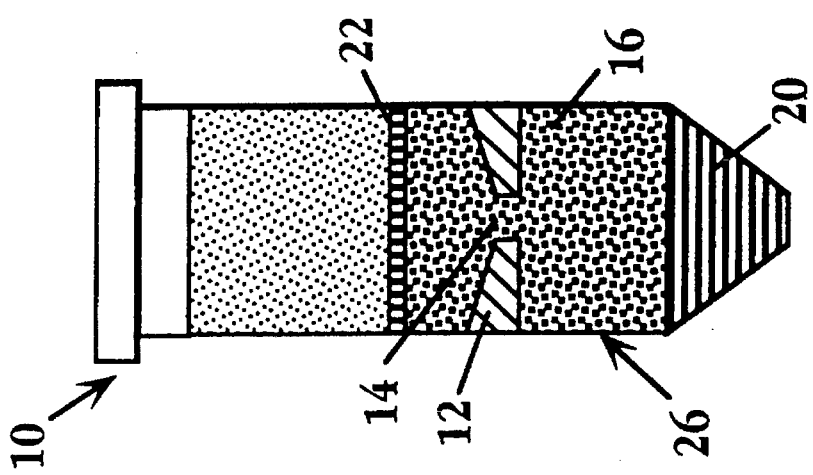
Figure 1A:
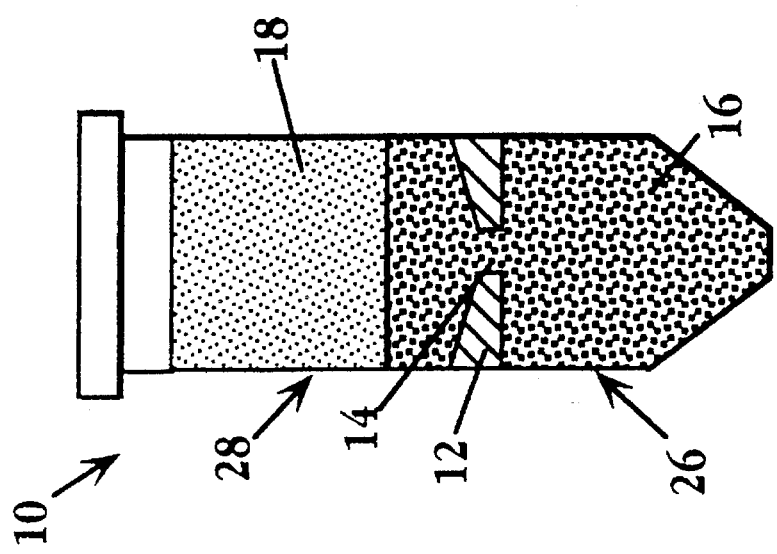

FIGS. 1A–C Cross-sectional views of a preferred embodiment of the centrifugation tube according to the present invention, illustrating the steps of isolating or separating cells according to the invention.

Figure 2A:
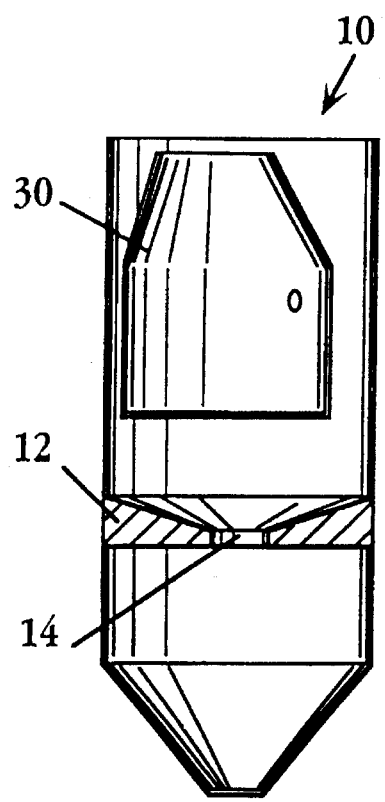

FIG. 2A A schematic cross-sectional view of an alternative preferred embodiment of the present invention.

Figure 2B:
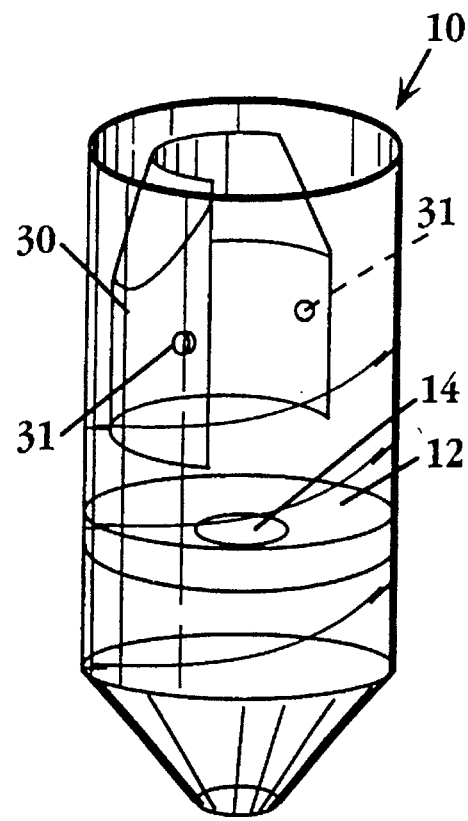

FIG. 2B A perspective view of the embodiment of FIG. 2A.

Figure 3:
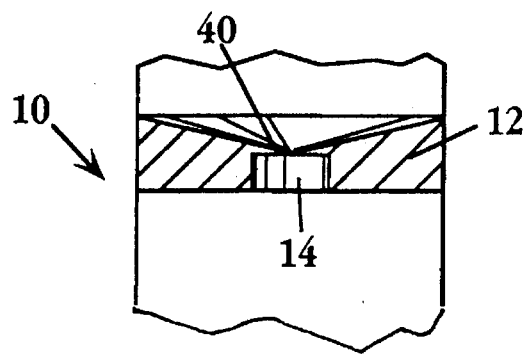

FIG. 3 A cross-sectional view of an alternative embodiment of the constriction member of the invention with a valve.

FIGS. 4A–E Examples of alterative shapes of the opening in the constriction member.

FIGS. 5A–F Cross-sectional views of alternative embodiments of the tube and constriction member of the invention.

FIGS. 6A and 6B Cross-sectional views of further alternative embodiments of the invention having multiple constriction members.

Figure 7:
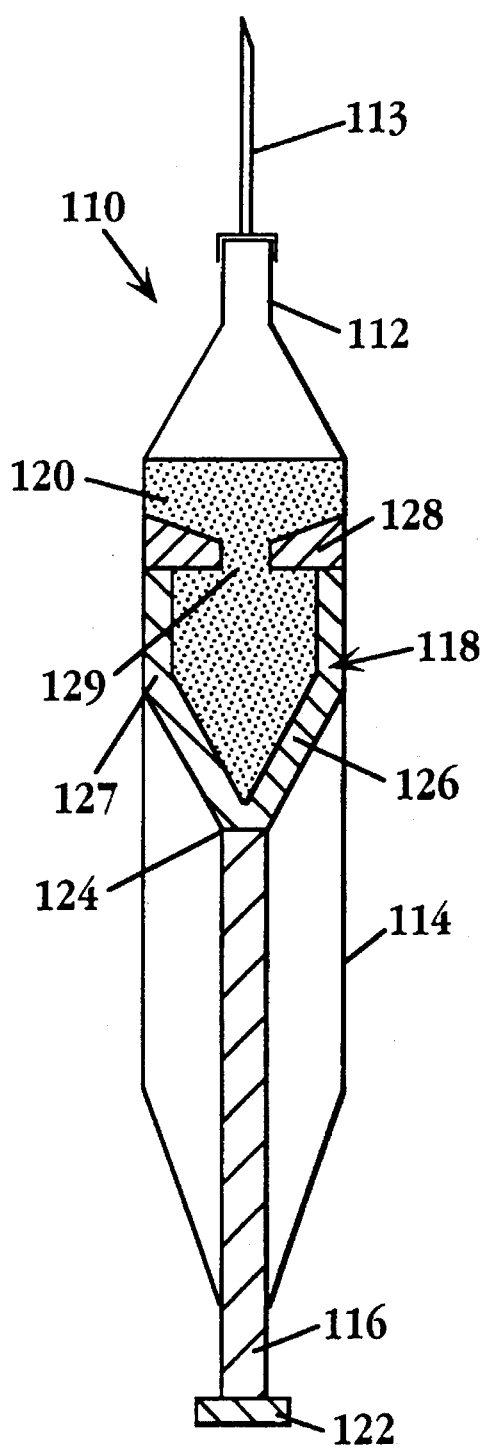

FIG. 7 A cross-sectional view of a centrifuge syringe before the extraction of a specimen.

Figure 8:
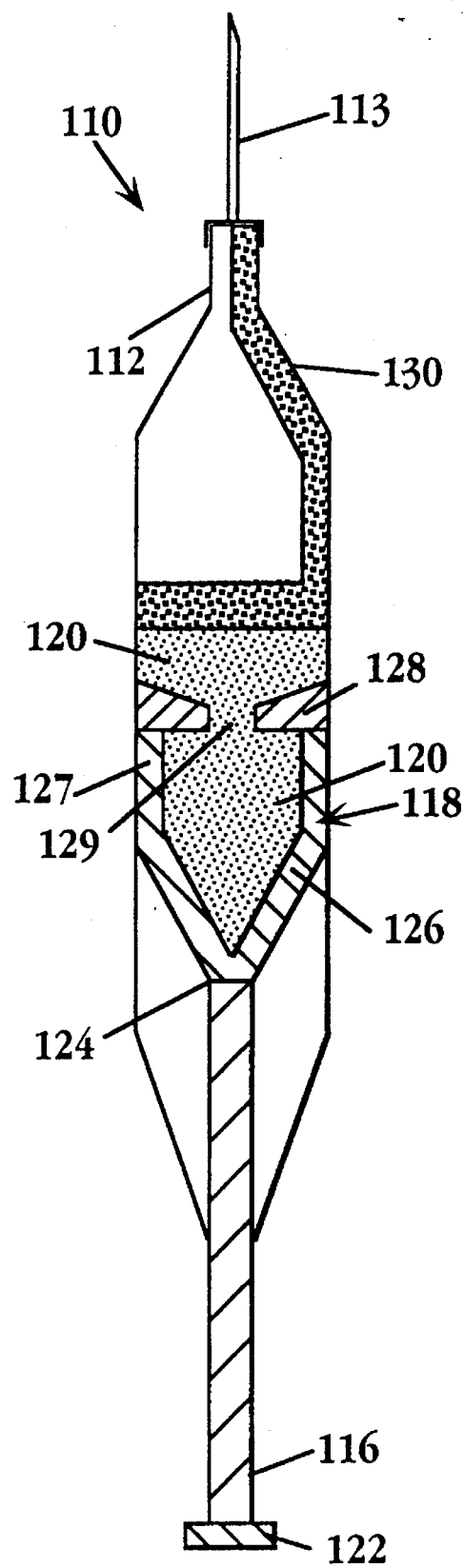

FIG. 8 A cross-sectional view of the centrifuge syringe of FIG. 7 upon introduction of the specimen.

Figure 9:
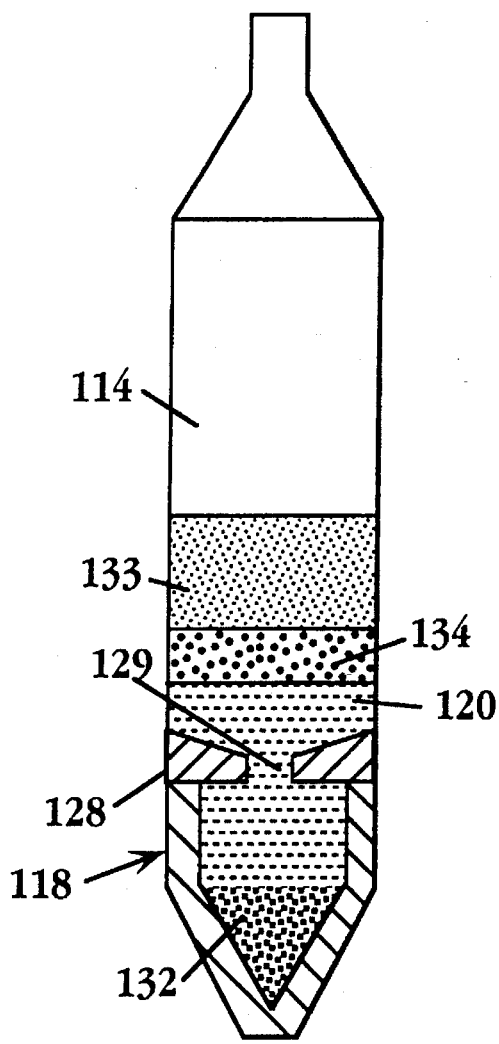

FIG. 9 A cross-sectional view of the centrifuge syringe of FIG. 7 after centrifugation.

Figure 10:
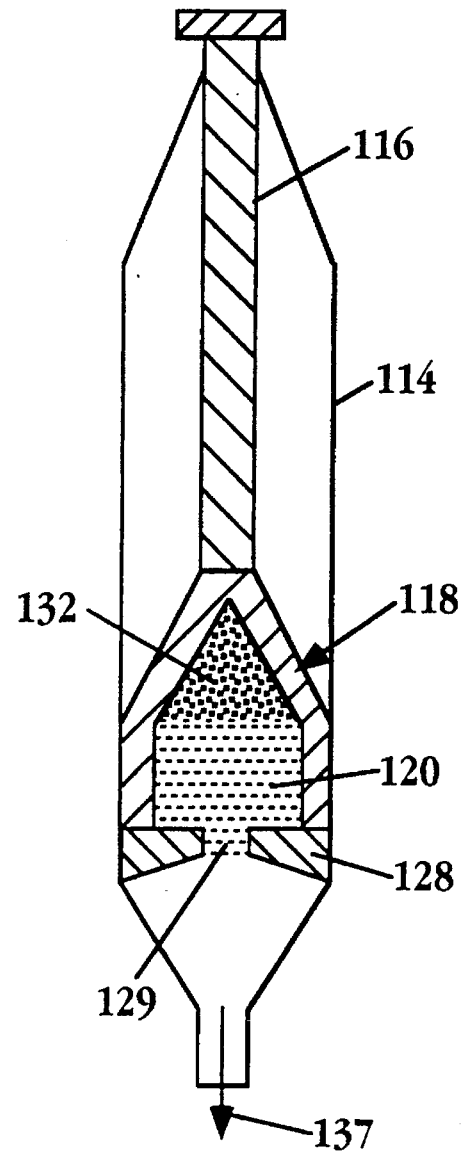
Figure 11A:
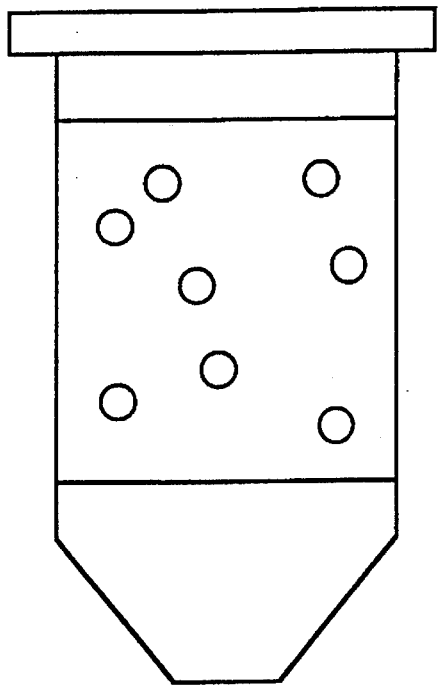
Figure 11B:
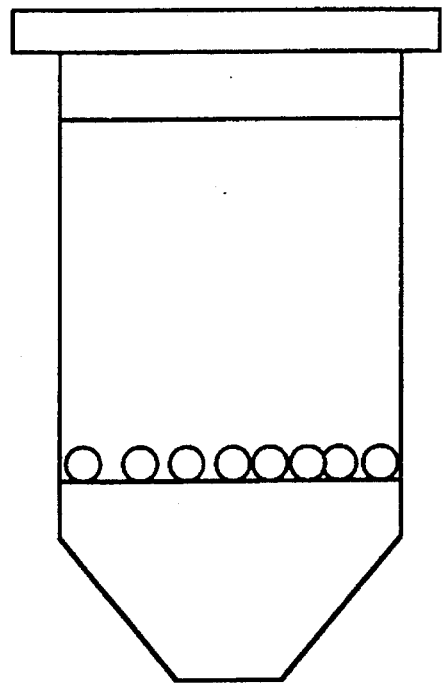
Figure 11C:
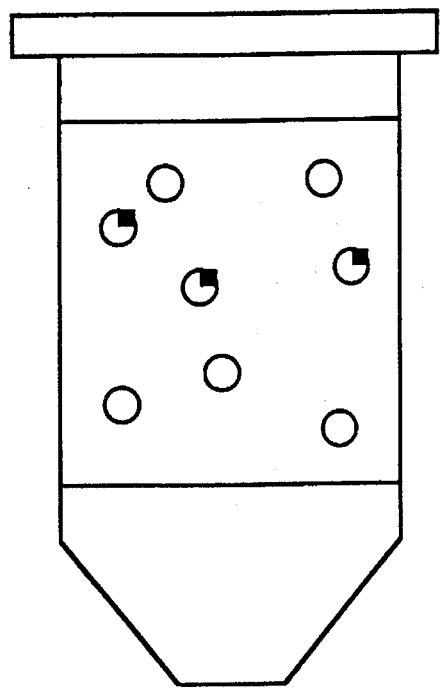
Figure 11D:
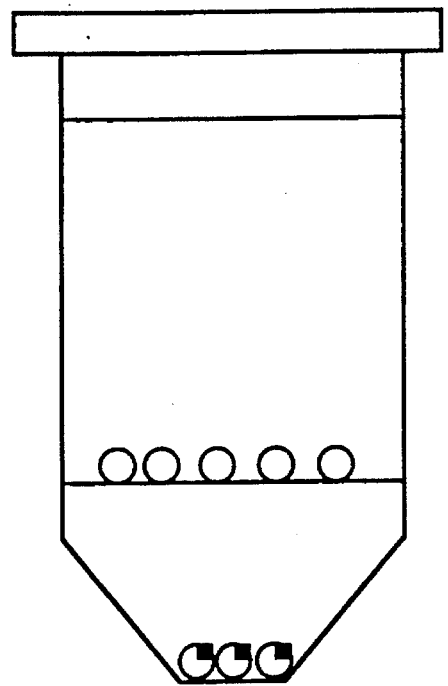

FIG. 10 A cross-sectional view of the centrifuge syringe of FIG. 7 upon removal of the specimen.

FIG. 11 A schematic drawing demonstrating the density adjusted cell sorting procedure.

Figure 12:
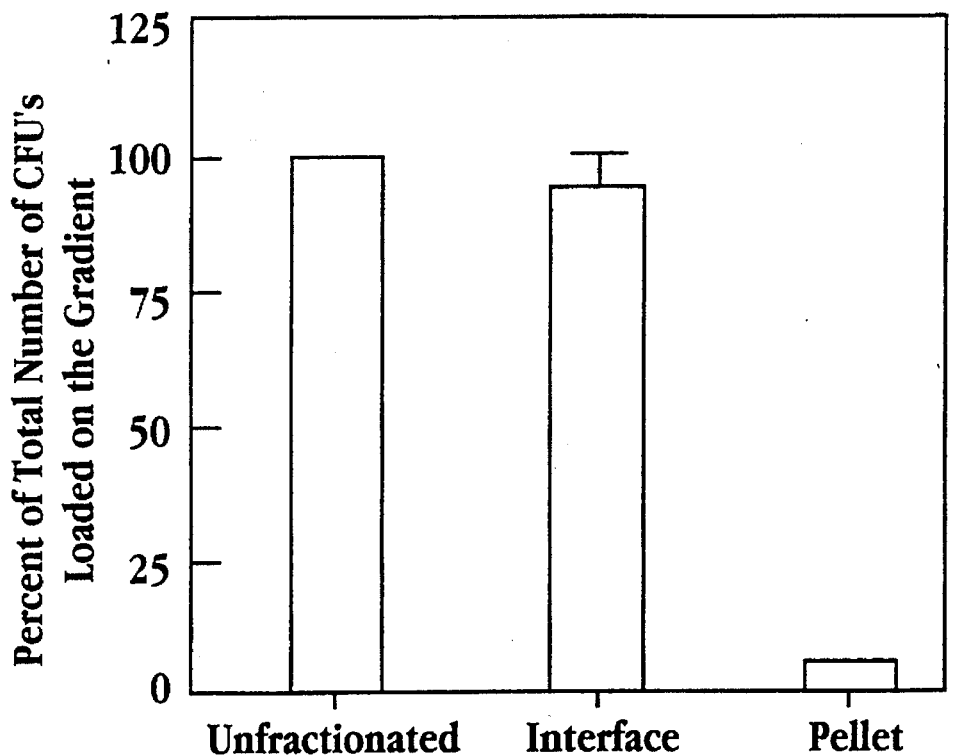

FIG. 12 Distribution of CFU's in interface and pellet fractions.

Figure 13:
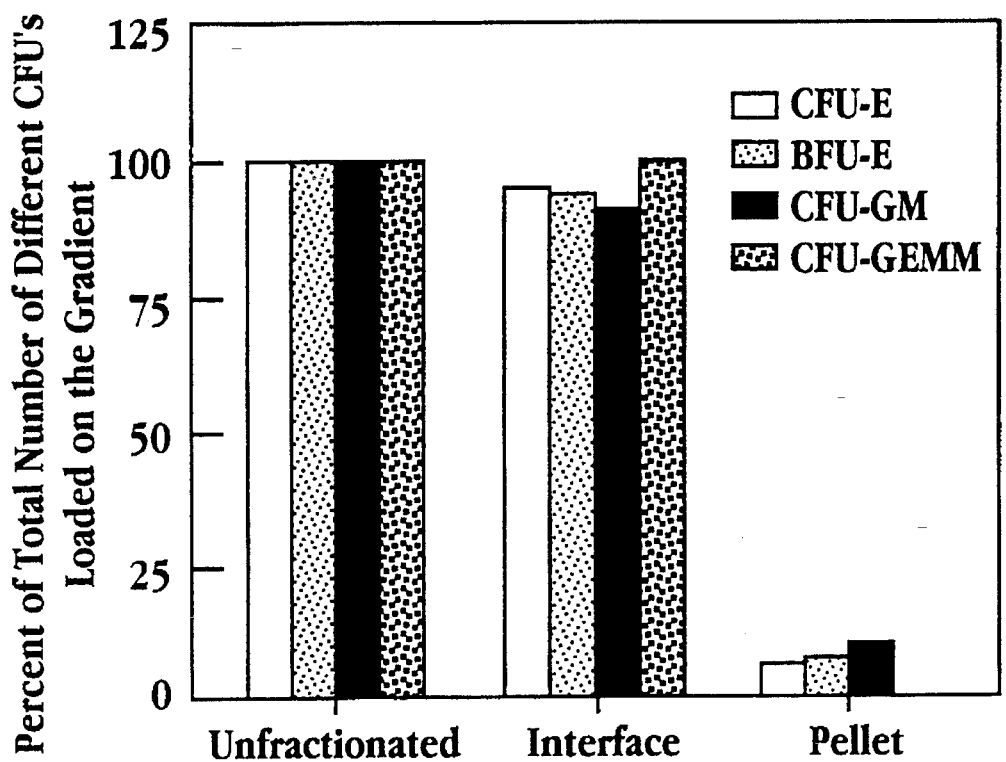

FIG. 13 Distribution of different types of CFU's in interface and pellet fractions.

Figure 14:
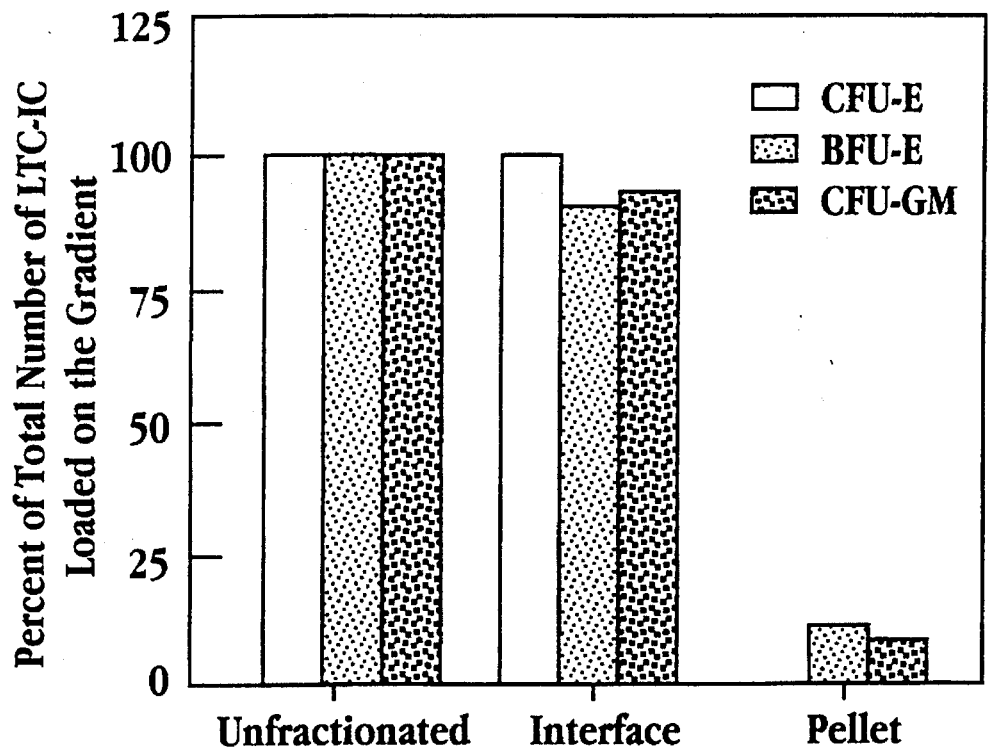

FIG. 14 Distribution of long-term culture initiating capability in interface and pellet fractions.

Figure 15:
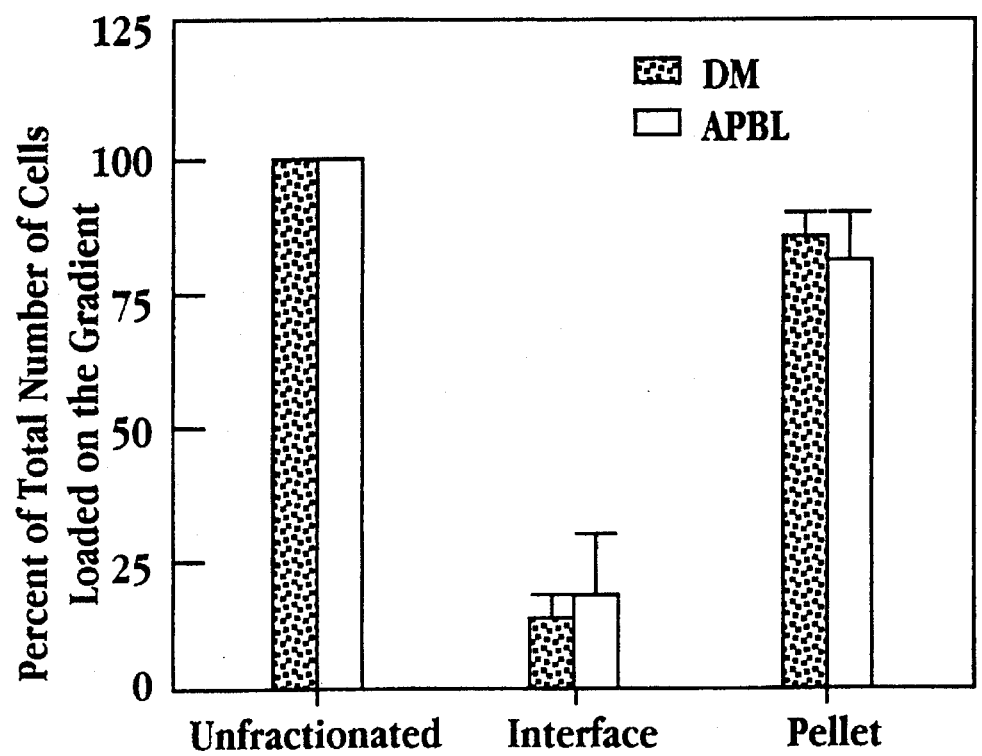

FIG. 15 Distribution of T cells in interface and pellet fractions.

Figure 16:
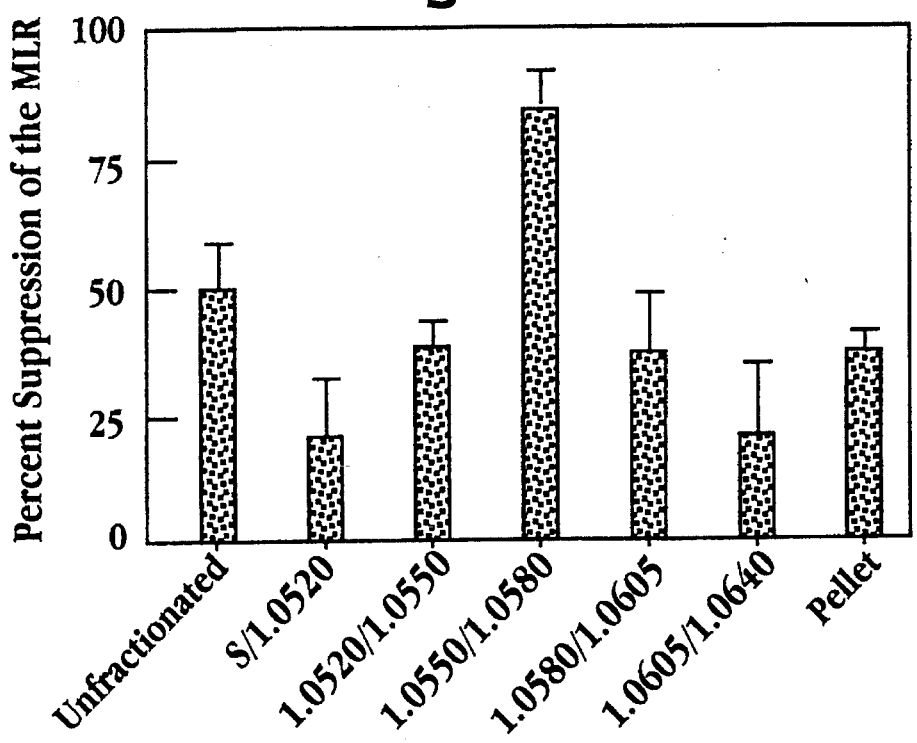

FIG. 16 Distribution of natural suppressor activity in different density fractions.

Figure 17:
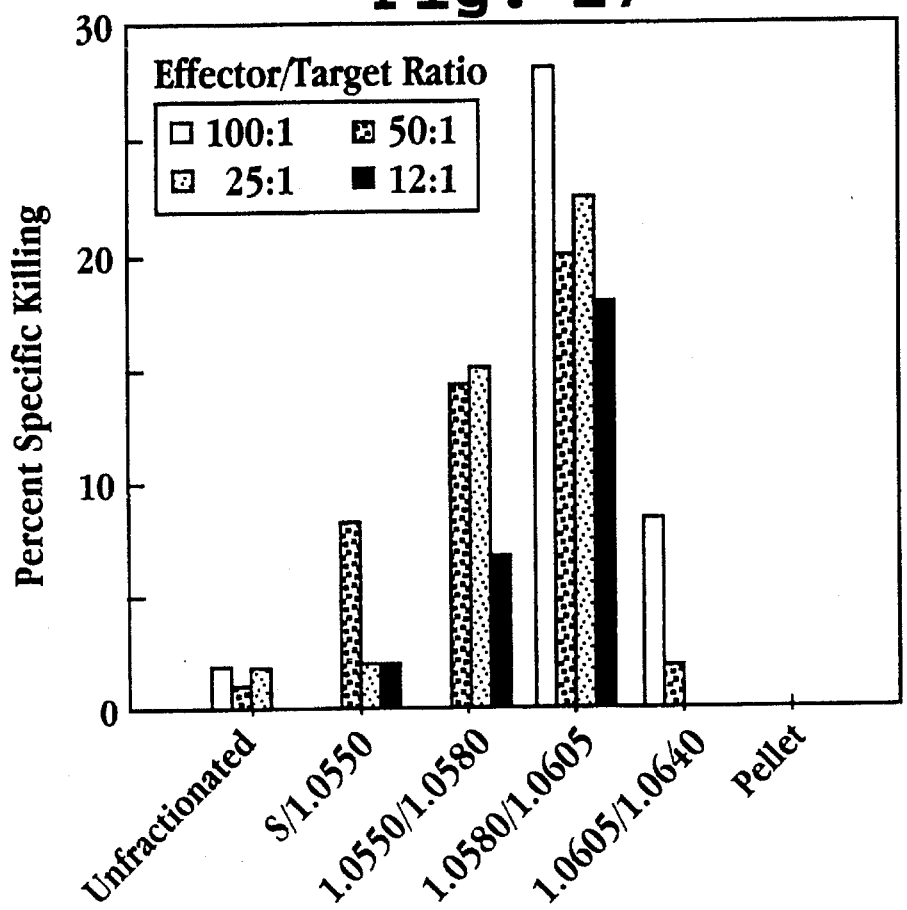
Figure 18A:
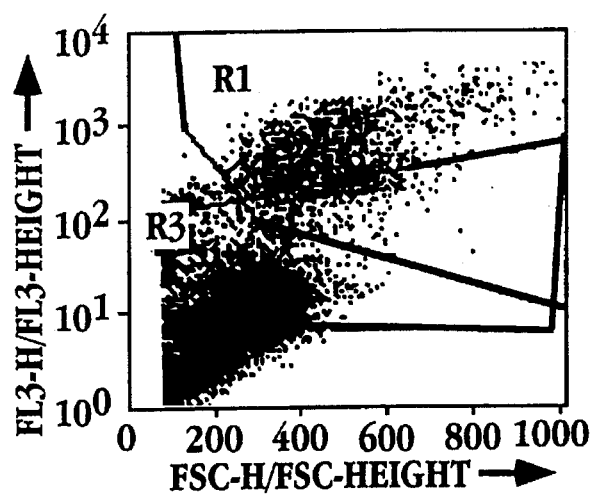
Figure 18B:
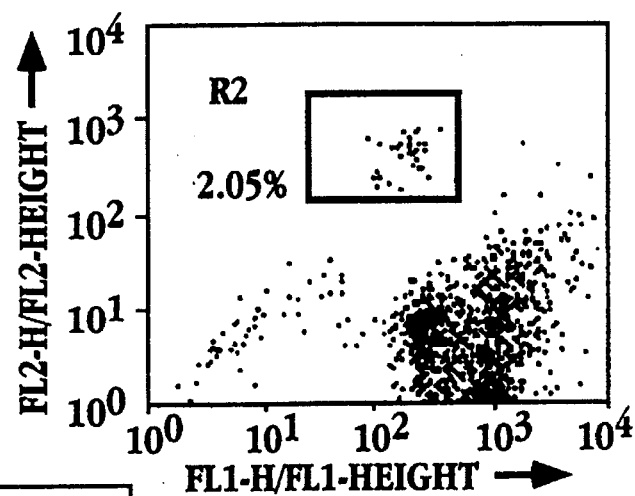
Figure 18C:
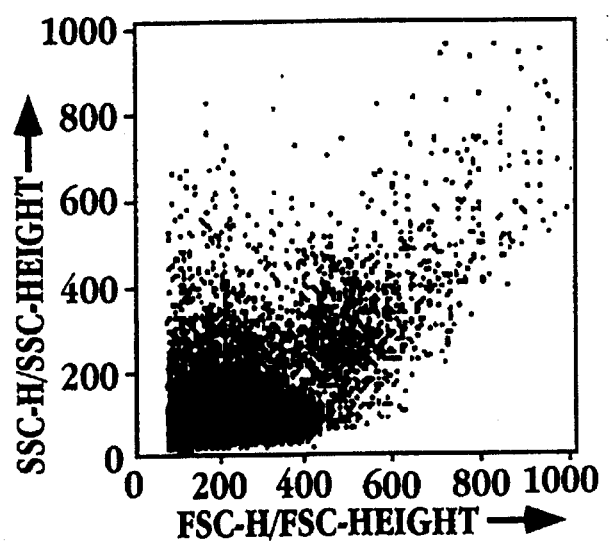
Figure 18D:
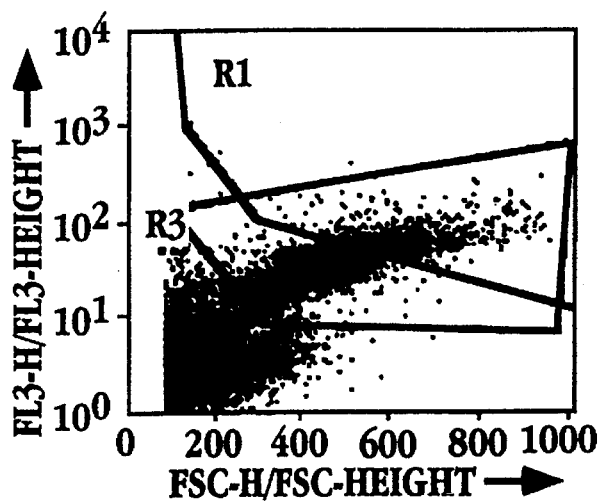
Figure 18E:
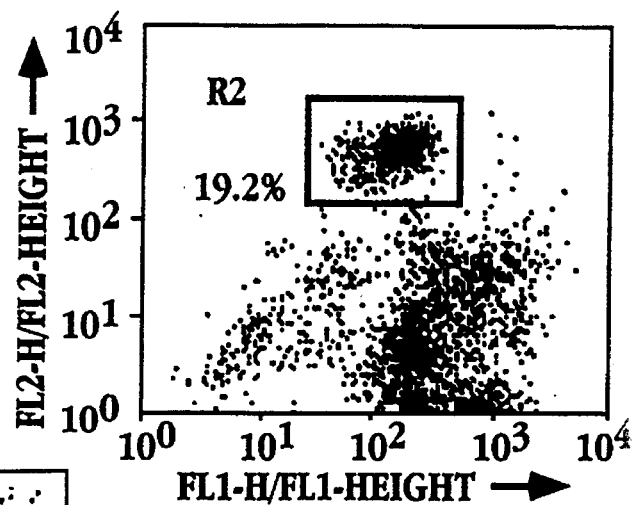
Figure 18F:
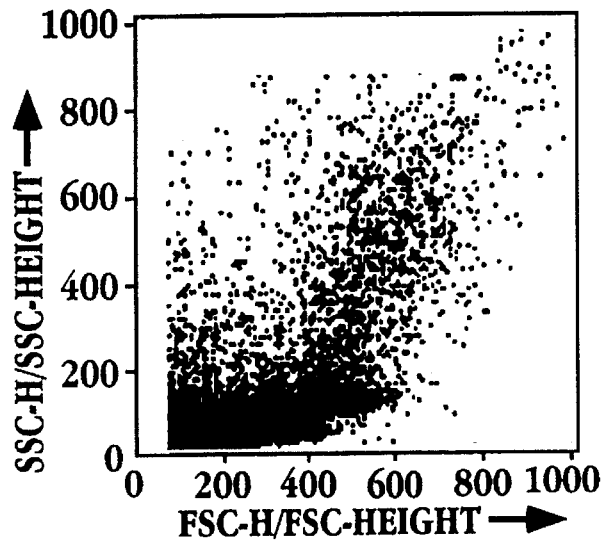

FIG. 17 Distribution of natural killer activity in different density fractions.

FIG. 18 Flow cytometric analysis of $CD34^+$ cell enrichment after density gradient centrifugation plus density adjusted cell sorting.

5. DETAILED DESCRIPTION OF THE INVENTION

5.1. Hematopoietic Progenitor Cells

Transplantation of bone marrow and peripheral blood is performed in the clinic for the treatment of cancer and hematopoietic disorders. The bone marrow and peripheral blood products are processed before being reinfused in the patients. One important step in this processing protocol is volume reduction, since it: 1) reduces the red blood cell mass, 2) reduces the amount of cryopreservatives needed to store the cells, 3) facilitates the removal of contaminating tumor cells (tumor purging) and 4) increases storage capacity.

A crucial clinical event following transfusion is the engraftment of the processed cell sample. This is largely dependent on the presence of hematopoietic progenitor cells in the processed product. Hematopoietic progenitor cells migrate to and reconstitute the bone marrow microenvironment after transfusion. Depending on their degree of differentiation these progenitor cells either contribute to short term engraftment or to long term engraftment of the bone marrow microenvironment.

In general cells which form differentiated erythroid, granulocyte, macrophage, megakaryocyte colonies contribute to short term engraftment. These colony forming cells (CFU) are unable to give rise to myeloid and lymphoid cells and therefore are unable to save the life of patients undergoing a therapy of lethal irradiation and chemotherapy. On the other hand, cells which form cobble-stone areas on irradiated bone marrow stroma layers and give rise to granulocyte/macrophage colony forming cells (CFU-GM) for at least five weeks in culture are considered cells with long term culture initiating capability (LTC-IC). LTC-IC are believed to provide long term engraftment of the bone marrow after transfusion in vivo. In other words, LTC-IC have the potential to provide long term progenies of the myeloid and lymphoid lineages, and therefore are able to rescue the life of patients by reconstituting the destroyed bone marrow.

In practice, CFU's provide short term bone marrow engraftment preventing infection in the patient during the time immediately following the radio- and chemotherapy. On the other hand, LTC-IC establish a long lasting, self-renewing myeloid and lymphoid system in the patient. It is currently believed that both the CFU and LTC-IC are necessary for successful transplantation and engraftment. Hematopoietic progenitor cells are characterized by the expression of the cell surface antigen CD34. The cell population expressing the CD34 surface antigen contains both CFU and LTC-IC. Hence, the present invention relates to methods for enriching total $CD34^+$ cells.

5.2. Enrichment of Progenitor Cells by Density Gradient Centrifugation

The present invention relates to methods of rapid and high yield enrichment of progenitor cells based on density gradient centrifugation. More specifically, the invention utilizes a precisely determined density of a density gradient solution contained within a specially designed cell-trap centrifugation tube to allow the $CD34^+$ cells to be collected by decantation in order to maximize cell yield. These steps are taken, because the number of progenitor cells in the starting cell mixture is usually very small, so that every effort directed to minimize cell loss during the cell separation process greatly enhances the accuracy of the subsequent use of the isolated cells.

A major advantage of the methods described herein is that a large volume of apheresed blood may be directly placed on the density gradient. Peripheral blood may be collected in anti-coagulant-containing tubes or by apheresis or leukopheresis. However, since the methods enrich progenitor cells based on their specific buoyant density, it is important that the cells are subject to separation within a relatively short time after their collection from an in vivo source because the density of the cells changes according to their culture or storage conditions. Therefore, in order to obtain optimal enrichment of progenitor cells from blood, it is preferred that the blood samples are used within 48 hours after their collection. Most preferably, blood samples should be subjected to density gradient centrifugation within several hours of collection.

The present invention demonstrates that proper adjustments of a gradient material to a specific density, osmolality and pH greatly enhance cell separation. For the enrichment of $CD34^+$ cells, a gradient should be adjusted to a density of 1.0605±0.0005 gr/ml, a physiologic osmolality of 270–290 mOsm/kg H2O and physiologic pH 6.8–7.8. In a specific embodiment by way of examples, apheresed blood from a cancer patient treated with G-CSF is directly loaded into a cell-trap centrifugation tube containing a "PERCOLL" solution filled to a level above the constriction, which has been adjusted to the preferred density of 1.0605±0.0005 gr/ml, osmolality of 280 mOsm/kg $H_2O$ and pH 7.4. The density of the "PERCOLL" solution may be adjusted on a densitometer to precisely define its accuracy up to at least the fourth decimal place. It should be noted that a variety of other gradient materials may be used to achieve progenitor cell enrichment, and they include, but are not limited to, "FICOLL", "FICOLL-HYPAQUE", cesium chloride, any protein solution such as albumin or any sugar solution such as sucrose and dextran. However, the density gradient solution should be prepared and adjusted to the appropriate density, osmolality and pH according to that disclosed herein, prior to its use. The gradient solution should be added to a centrifugation tube in a volume sufficient to allow all the cells having a higher density to pass through the gradient during centrifugation. For example, a volume of about 20–25 ml of the solution is generally adequate for separating cells in 20 ml of apheresed blood samples.

Any tubes suitable for use in centrifugation may be used for the practice of the invention. In a preferred embodiment, the present invention is directed to a cell-trap tube for the density separation of $CD34^+$ cells. For the purpose of the present invention, a cell-trap tube refers to a centrifugation tube which contains within it a constriction or a trap and a properly adjusted density gradient material filled to a level above the constriction so that cells having a certain density pass through the opening of the constriction to form a cell pellet in the compartment below the constriction during centrifugation.

Figure 4A:
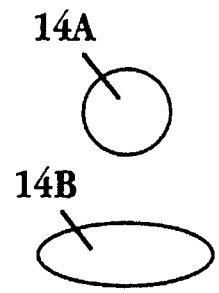
Figure 4B:
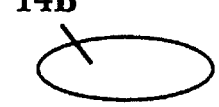
Figure 4C:
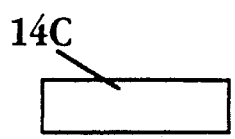
Figure 4D:
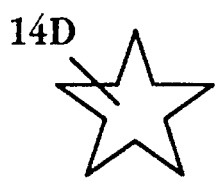
Figure 4E:
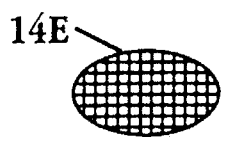

According to a preferred embodiment shown in FIGS. 1A & B, tube 10 includes constriction member 12, which defines central opening 14. The upper surface of constriction member 12 is preferably slightly angled inward, toward opening 14. The bottom surface of the constriction member also may be similarly, slightly angled (although not shown as such in the figures). In an exemplary embodiment, with a tube having an inner diameter of about 2.8 cm, the diameter of opening 14 formed by constriction member 12 is preferably about 0.5 cm. The size of opening 14 is generally not so small as to prevent heavier components of a sample, layered on top of the density gradient solution, from passing through the opening prior to actual centrifugation. Such a movement of components may occur due to normal gravitational forces. In general, the diameter of opening 14 is dictated by the ability to form an increased surface tension across the opening. A restriction that is little more than a rim around the interior of the barrel may be sufficient. Hence, the cross-sectional area of the aperture formed by the constriction member may be as little as about 5% or as great as about 95% of the horizontal cross-sectional surface area of the tube. In addition, the annular member may consist of a mesh or a sieve spanning the horizontal cross-section of the tube. In this case, the annular member is said to comprise a plurality of openings, such as illustrated in FIG. 4E.

Tube 10 is filled with density gradient solution 16 to a level above constriction member 12, or at least above opening 14. Preferably, with reference to a standard 50 ml centrifugation tube, density gradient solution 16 is filled to a level at least about 1 mm above the constriction member. The fluid sample to be separated is layered on the top of the density gradient solution, and the tube and its contents are subjected to centrifugation. Preferably, the sample is carefully layered so that at least about 1 mm of density gradient solution remains between the sample and the top of the constriction member after layering.

Referring to FIG. 1B, following centrifugation, components having densities greater than that of the gradient solution are found in a pellet 20 at the bottom of tube 10. Components having densities less than that of the density gradient solution remain floating at the top of the solution, in an interface 22 between the gradient solution and the remaining portion of the fluid sample solution. The interface portion is then poured off as indicated by arrow 24 in FIG. 1C. The provision of the density gradient solution to a level above the opening as described above helps to prevent the formation of an interface portion below constriction member 12.

Constriction member 12 facilitates pouring off the upper portion by providing a support or nucleus for formation of an intermediate surface tension across the surface of opening 14 when tilted for pouring. This surface tension impedes mixing of upper and lower portions of the tube when the contents of the upper portion are poured out of the tube. Constriction member 12 may be provided as an insert placed into a straight-walled tube. Alternatively, constriction member 12 may be formed as constriction of the tube wall during a molding process in the making of the tube itself. When the constriction member is provided by an insert, the insert may be movable to enable the operator to change the relative volumes of the lower portion 26 and upper portion 28 of tube 10 according to experimental conditions. The position of the constriction member in a molded tube can also be varied, during the manufacturing process, to provide tubes of differing relative upper and lower portion volumes. For example, in the isolation of cells from peripheral blood, a 20 ml sample of blood requires lower portion 26 to be about 15 ml in order to accommodate the relatively large amount of red blood cells centrifuged out. By comparison, a 20 ml sample of apheresis or buffy-coat blood would require only about 10 ml in the lower portion.

In many applications, it will be desirable to collect only the supernatant fraction containing the interface portion. In such cases, the pellet is discarded with the tube. In other cases, the pellet can be removed by mechanical manipulation/disruption. For example, the tube can be inverted and subjected to vortex mixing. Such mixing will disrupt the pellet into the adjacent liquid phase and will induce movement of this liquid phase and disrupted cells from the lower or collection portion of the tube into the upper portion of the tube.

An advantage of the present invention is that the low density material above the constriction member is separated from material beneath by the simple act of pouring. This contrasts with many conventional methods of unloading gradient separations using standard straight-wall centrifuge tubes, where materials are separated by carefully pipetting out of the tube or, alternatively, by puncturing the bottom of the tube and allowing the contents of the tube to slowly drip out into collection vessels. Thus, the present invention provides a convenient, simple means for unloading differentially separated materials. In addition, unlike conventional straight-wall tubes, if the centrifuge tube of present invention is dropped or accidentally inverted, the contents will not readily mix due to the presence of the constriction member. Moreover, once separation has taken place, the solution present above the constriction member can be mixed in the tube, without disturbing (or fear of contamination by) the contents of the tube below the constriction member.

In an alternative preferred embodiment, tube 10 may be provided with insert or shield 30, as shown in FIGS. 2A and 2B. Shield 30 is provided above constriction member 12 to facilitate layering of the sample onto the gradient solution. Shield 30 may take the form of a roughly concentric insert placed in the upper portion of the tube and extending at least partially around the tube. In use, the operator pipettes material between shield 30 and the tube wall. The shield directs the material along the side of the tube to the top of the density gradient solution, while minimizing disturbance of the solution. As shown in FIG. 2B, tube 10 is a clear plastic or glass, with constriction member 12 formed as a separate silicone insert. Shield 30 can be held in the upper portion of the tube, for example, by interference fit with spacers 31 biasing against the tube wall. Alternatively, shield 30 could be formed as a part of the tube.

The separation of materials may be further enhanced by the addition of valve 40 to the constriction member, as shown in FIG. 3. The valve 40 is located across opening 14. Valve 40 may be a one-way valve, or a valve that only opens upon application of a threshold centrifugal force. The valve can be formed by providing flaps of a softer material over the opening. In a preferred embodiment, the force required to open valve 40 would be about 850 times the normal force of gravity. Valve 40 thus allows heavy cells to pass through during initial centrifugation, and then keeps those cells in place, allowing for further processing of the lighter cells of interest located above the valve (such as washing or mixing of the cells). In this way complete and final manipulation of the cells can be performed in a single sterile container.

The shape of opening 14 is not limited to a circular shape, though in general, a funnel-shaped restriction forming a roughly circular shape 14A will be preferred. As shown in FIGS. 4A–D, the opening may also be oval 14B, rectangular 14C, star-shaped 14D, or any other shape that would create a restriction.

FIGS. 5A–F are illustrations of alternative shapes and designs for the tube and constriction member according to the invention. FIG. 5A shows alternative tube 42 having a separate bottom compartment 44 for receiving the pellet to provide optimal collection of cells. Constriction member 12 is as previously described; it is funnel shaped on its upper surface and formed from a separate insert of plastic or, preferably, silicone. FIG. 5B shows a tube 46 with a pointed bottom wall. Tube 46 with the pointed bottom wall also enhances cell collection by allowing the heavier cells to form a better pellet, which may be desired if the cells are to be collected. Constriction member 48 is again an insert, but with a flat upper surface and wider opening. FIG. 5C illustrates alternative tube 50 with an integrally molded constriction member 52. FIG. 5D shows an alternative constriction member 54 that facilitate movement within tube 55 to adjust the relative volumes of the upper and lower portions. For this reason constriction member 54 has annular extendings contact points 56. The constriction member will only contact the tube at these points, which create a fluid tight seal, but allow for easier adjustability. Tube 55 also has a flat bottom. FIG. 5E illustrates a further alternative embodiment of the present invention, wherein tube 60 includes cell trapping material 62, such as a sponge or gel. Material 62 may contain compounds that specifically bind certain cell types or toxins that kill specific cell types. Material 62 also may be made of a magnetic material if desired. Tube 64, shown in FIG. 5F, illustrates a further example of an integrally formed constriction member 66 in a tube with a flat bottom wall 68. Construction member 66 is located such that lower portion 26 has a smaller relative volume.

FIGS. 6A and B illustrate further alternative embodiments of the tube according to the invention. In each, two constriction members are provided. Second constriction member 12A is located above first constriction member 12B to create more compartments to allow separation of cells of differing densities. In FIG. 6A, the constriction members are shown as separate inserts, whereas they are integrally formed with the tube in FIG. 6B. Additional constriction members could also be added if a sample of several different densities is to be separated.

It will be applied by persons of ordinary skill in the art that the embodiments of FIGS. 2–6 are illustrated herein without density gradient solution for the sake of clarity only. Preferably, each embodiment would contain density gradient solution as described herein in connection with the embodiment of FIG. 1A.

In a preferred embodiment, the cell-trap tube may be used in the form of a centifuge syringe, which is a completely enclosed system to ensure sterility.

One embodiment of centrifuge syringe 10 according to the invention is illustrated in FIG. 7. The centrifuge syringe 10 includes a specimen container 14 with a central orifice surrounded by fitting 12 adapted for receiving a needle 13, a handle 16 and a plunger 18. Fitting 12 may be any type of locking tip adapted to hold a needle, for example, a Luer-Lock™ syringe tip. Alternatively, fitting 12 may be a sterile septum adapted for connection with sterile fluid bags and tubes, for example a SAFSITE™ small wire extension set with reflux valve and Spin-Lock™ adaptor available from Burron Medical Inc., Bethlehem, Pa.

Handle 16 further preferably comprises knob 22 and a removable connection 24 to plunger 18. As shown in FIGS. 7–10, plunger 18 is single piece, machined or molded from a plastic material. Known medical grade plastic materials may be used. The plunger preferably has a funnel-shaped bottom wall 26 that is removably connected to the handle at connection 24. Side wall 27 preferably closely matches the container wall to permit sliding movement but provide an essentially fluid-tight barrier therearound. A top wall is formed by constriction member 28, which defines central opening 29. Alternatively, the outer diameter of side wall 27 may be slightly undersized to facilitate sliding and an o-ring seal provided between side wall 27 and container 14. Removable connection 24 may take the form of, for example, a screw fitting or a snap-fit. Preferably, connection 24 also provides for reattachment of handle 16. If reattachment is not desired, connector 24 may be designed such that handle 16 can be broken off. A suitable connection can be selected by those of ordinary skill in the art.

The plunger 18 is filled with a density gradient material 20 before the introduction of a specimen. Preferably, the density gradient material is filled to a level above the constriction member, or at least above the top of opening 29. For example, when using a standard 50 ml syringe, having an inner diameter of about 2.8 cm, the gradient material is preferably filled to a level about 1 mm or more above constriction member 28. This fill level will help to prevent the formation of an interface portion, as explained below, under constriction member 28.

Referring to FIG. 8, the introduction of the specimen into centrifuge syringe 10 is illustrated. Specimen 30 is drawn into the syringe through needle 13 secured to fitting 12, aided by the vacuum created by handle 16 and plunger 18 as the handle is pulled out of container 14, drawing the plunger away from fitting 12. The handle should be pulled with sufficiently low force and velocity to avoid mixing of the specimen with the density gradient material onto which the sample is layered. Preferably, when the handle is pulled at an appropriate force, the sample will form a stream which adheres to the side of the container as it is drawn in, as shown in FIG. 8. This will reduce unwanted mixing. Mixing of the two materials is also minimized by the fact that the density of the specimen is significantly lower than the density of the density gradient material. After specimen 30 is drawn into container 14, the container is maintained in an upright position and the sample lies on top of density gradient material 20.

Using needle 13, a sample such as peripheral blood may be drawn directly from a patient for analysis. The present invention thus ensures sterility of such a sample by completely eliminating direct handling of the sample prior to introduction into the centrifugation container. Alternatively, using a sterile septum, blood previously collected by known techniques and stored, for example in a sterile bag, may be drawn into the centrifugation container through sterile tubing or other known sterile connection means. The present invention thus ensures a sterile transfer of sample material on a larger scale in a completely closed system, again without direct handling of sample material.

Once the specimen has been completely drawn into the container 14, and the handle 16 has been pulled so that the removable connection 24 is located at the central orifice of the specimen container 14, the handle 16 can be removed for the centrifugation step.

FIG. 9 illustrates the centrifugation syringe after the centrifugation step has been performed. As shown, the handle 16 has been detached from the plunger 18, which is located at the bottom end of the container 14. Centrifugation of container 14 results in a pellet 32 being formed from the heavier portions of the specimen at the bottom of the plunger 18. Density gradient material 20 is located above pellet 32. An interface portion 34, which contains the cells of interest, is formed between specimen diluent 33 and density gradient material 20, and above constriction member 28.

Interface portion 34 may be removed from the centrifuge syringe 10 by inverting the centrifuge syringe and ejecting it off as indicated by arrow 37 in FIG. 10. Further removal of density gradient material 20 and the pellet 32 can be facilitated by reattaching handle 16 to plunger 18 at connection 24. The handle then can be pushed into the container to aid the removal of the material if necessary.

5.3. Density Adjusted Cell Sorting

Density gradient centrifugation is a method of separating cells based on the different densities of cell types in a mixture. The method is often used in a single step to separate cells into two compartments which contain cells that are either lighter or heavier than a specific density of the gradient material used. However, due to the imprecision of the procedure, the use of a single density usually does not allow the cells of interest to be enriched to a significant level of purity, especially if the cells are present in a low number among many undesired cell populations. Thus, density gradient centrifugation is most often carried out through repetitive steps based on a series of different density gradients or in combination with affinity chromatography, cell panning, cell sorting, and the like. Alternatively, discontinuous density gradient centrifugation may be performed using multiple layers of the different gradient densities. This method allows cells of different densities to form zones or bands at their corresponding densities after centrifugation. The cells in the different zones are then collected by placing a pipette at the appropriate location. Such a method is difficult to carry out in a routine manner in a clinical setting because it requires skilled personnel for the preparation of the gradient, and there is often mixing between the different layers of the density solution before and/or after centrifugation that potentially disrupts cell separation. Most importantly, the above-described procedures require multiple steps that unavoidably cause substantial cell loss, thus they are not amenable for the separation of cells present in a low number within a mixture in a routine manner.

The present invention circumvents these problems by combining density gradient centrifugation and affinity cell separation into a single method referred to as density adjusted cell sorting. This method modifies the conventional positive and negative selection by solid phase binding methods, and combines it with the specific density of $1.0605 \pm 0.0005$ gr/ml for $CD34^+$ cell separation. FIG. 11 demonstrates the use of density adjusted cell sorting as compared to conventional density gradient centrifugation. While the conventional methods are able to concentrate many irrelevant cell types to form a pellet, there are still a large number of undesired cell types trapped at the interface with the cells of interest. However, density adjusted cell sorting provides for the use of cell type-specific binding agents conjugated to heavy carrier particles with specificity for antigens expressed by the undesired cell populations, and incubating such agents with the cell mixture prior to centrifugation, so that such density-adjusted cells would be pelleted during centrifugation. Thus, although these cells are normally lighter than the gradient density, a heavier density is imparted to them due to the higher density of the carrier particles which are rendered cell type-specific by the antibodies used. When density adjusted cell sorting is applied to a cell mixture which is overlaid onto a customized density gradient contained within a cell-trap centrifugation tube, a single centrifugation step allows for substantial enrichment of a cell type of interest from any cell mixture.

Example 6, infra, shows that aphaeresed blood from cancer patients could be directly incubated with carrier particle-coated-anti-CD45 antibodies which react with most leukocytes. Since $CD34^+$ cells express low levels of the CD45 antigen, the vast majority of the non-$CD34^+$ cells are rendered heavier than the density material and pellet during centrifugation. A variety of such cell type-specific binding agents may be used to target specific cell types in the blood. These agents encompass antibodies such as the leukocyte-specific antibodies, e.g., anti-CD3, anti-CD4, anti-CD5 and anti-CD8 specific for T cells; anti-CD12, anti-CD19 and anti-CD20 specific for B cells; anti-CD14 specific for monocytes; anti-CD16 and anti-CD56 specific for natural killer cells; and anti-CD41 for platelets. Many of these antibodies are commercially available in a form already conjugated to various types of particles (AMAC, DYNAL). In addition, cell type-specific binding agents include lectins such as wheat germ agglutinin and soy bean agglutinin, growth factors and cytokines. Alternatively, a positive selection procedure may be used to cause the $CD34^+$ cells to be heavier than their normal density so that they are pelleted during centrifugation. In this case, antibodies directed to CD34 coated on carrier particles are used to pellet all remaining $CD34^+$ cells. Furthermore, antibodies directed to any cell surface marker may be directly linked to heavy particles for use in density adjusted cell sorting, following conjugation methods well known in the art. It is noteworthy that when density adjusted cell sorting is applied, the specific density of the gradient is less critical, as long as the undesired cells are all rendered heavier. Although the methods of the present invention do not provide for the isolation of $CD34^+$ cells to absolute purity, they allow the cells to be enriched substantially without major loss of $CD34^+$ cells so as to enhance their subsequent use.

A number of commercially available carrier particles may be used in the present invention and include, for example, organic polymers, e.g. polyethylene; polypropylene; polyvinyl compounds e.g., polyvinylchloride, polyacrylonitrile, polyacrylate, polymethacrylate, polycarbonate and copolymers thereof; polystyrene latex; nylon; polyterephthlate; and the like, or inorganic polymers, e.g. glass or silica particles; cellulose, polysaccharides, e.g. agarose, cellulose, Sepharose, Sephadex, etc., or combinations thereof. The carrier particles may be from naturally occurring polymers, modified naturally occurring polymers and synthetic addition and condensation polymers. A preferred carrier particle of the present invention is a silica particle between 0.1–5.0 microns coupled to an aminopropyl group and having a density of greater than 1.08 gr/ml. U.S. Pat. Nos. 4,927,750 and 4,927,749, issued May 22, 1990, describe examples of modified silanes which may be used in the present invention as carrier particles. Various carrier particles are commercially available from, for example, Bangs Laboratories, Inc., Carmel, Ind., Pharmacia, Sigma Chemical Company, Bio-Rad, AMAC, Inc., etc. A preferred heavy carrier particle of the present invention is one having a density greater than 1.08 gr/ml and a particle size of 0.1 micron to 5.0 micron such that the carrier particles will be pelleted upon centrifugation, as well as one having the capability of binding, either directly or indirectly to cell-type specific binding agents.

Immobilization of a cell-type specific binding agent to carrier particles can be achieved by a variety of techniques known to those skilled in the art. Such techniques are described in, for example Bangs (*The Latex Course* (1992), available from Bangs Laboratories, Inc. Carmel, Ind.) Yoshioka et al. (*Journal of Chromatography*, vol. 566, pp. 361–368 (1991); Pope et al. (*Bioconjugate Chem.* (1993) 4:166–171); Harlow and Lane 1988 (*Antibodies: A Laboratory Manual,* Colorado Spring Harbor Laboratory). *Avidin-Biotin Chemistry: A Handbook,* 1992, ed. Savage et al., pub. PIERCE; Hermanson et al., *Immobilized Affinity Ligand Techniques,* 1992, pub. Academic Press, Inc. Binding techniques include, for example, simple physical absorption or adsorption where the cell-type specific binding agent is bound directly to the carrier protein without the use of functional groups; complex adsorption where a second binding agent, e.g. BSA, is coadsorbed to the carrier particle and forms the basis for binding functional groups; and covalent bonding of the binding agent to the carrier particle. The biotin-strepavidin affinity system may also be used in the present invention to bind cell-type specific binding agents to the carrier particles. Various particle surface chemical reactions for covalent coupling are known to those of skill in the art and include, but not limited to, carboxylic acid, primary or aliphatic amine, aromatic amine or aniline, chloromethyl (vinyl benzyl chloride), amide, aldehyde, hydroxyl, thio, hydrazide, epoxy, sulfate and sulfonate. Other coupling chemical reactions are described in Bangs, Uniform Latex Particles (1984).

In the present invention, it is preferred that the direct or indirect binding of the cell-type specific binding agent to the carrier particle be performed in excess binding agent to allow for maximum coverage of the surface of the carrier particle, thereby reducing the potential for non-specific binding. Carrier particles may also be subjected to blocking agents, e.g. casein, gelatin and Tween to fill any unoccupied sites on the carrier particle in order to reduce non-specific binding.

In one illustrative example of a coupling reaction, carboxyl groups on the carrier particle surface can be made reactive with the available amino groups on the cell-type specific binding agent. Other means of binding cell-type specific binding agent to particle surfaces include employing activated carboxylic acids, carbodiimides, i.e. (1-ethyl-3-(3-dimethylaminopropyl) carbodiimide or EDAC, imido esters, active alkyl halides, etc., to form amido, amidine or amino linkages.

A preferred carrier particle of the present invention is an aminopropyl silica particle wherein the amino groups have been coupled to the silica particle through a glutaraldehyde linkage.

6. EXAMPLE

Enrichment of $CD34^+$ Cells from Blood Cell Mixture

6.1. Materials and Methods

6.1.1. Peripheral Blood and Bone Marrow

Aphaeresed peripheral blood was applied directly onto the density gradient. However, complete blood and bone marrow aspirates were processed to a buffy coat (removal of red cells) before they were applied onto the density gradient.

Patients were hydrated and treated with cyclophosphamide (4 gm/m$^2$) administered by intravenous (IV) infusion over two hours through a central venous catheter. Twenty-four hours after the completion of the cyclophosphamide infusion, patients are treated with G-CSF (Neupogen, Amgen, Thousand Oaks, Calif.) administered by subcutaneous (SC) injection at a dose of approximately 10 µg/kg/d. Apheresis was initiated upon recovery of the white blood cell count (WBC) to equal or more than $1 \times 10^9$/L. Apheresis was performed using a Cobe Spectra Cell Separator (Lakewood, Colorado) at a rate of 80 ml/min for 200 min (total volume of 16 L).

6.1.2. Preparation of Density Gradients

"PERCOLL" solution was purchased from Pharmacia Biotech (Uppsala, Sweden) and stored at 4° C. according to the recommendation of the vendor. A stock solution was prepared by mixing 12 parts of "PERCOLL" with 1 part of 10×calcium and magnesium-free phosphate buffered saline (PBS). The pH of the solution was adjusted to 7.4 and the osmolality to 280 mOsm/Kg H$_2$O. For use in separating CD34$^+$ cells in a cell mixture, the stock solution was further diluted with calcium and magnesium-free PBS to a density of 1.0605±0.0005 gr/ml and used at room temperature. It was crucial to adjust the density of the gradient to an accuracy of within ±0.0005 gr/ml of 1.0605 gr/ml in order to ensure reproducibility and accuracy of cell separation. This was done by a high precision digital density meter such as DMA 48 (Anton PAAR U.S.A., Ashland, Va.). All procedures were performed under sterile conditions and at room temperature.

6.1.3. Density Gradient Centrifugation of Aphersed Blood and Bone Marrow Buffy Coats Apheresed blood or bone marrow buffy coat samples were layered on a "PERCOLL" gradient previously adjusted to a density of 1.0605±0.0005 gr/ml, an osmolality of 280 mOsm/Kg H$_2$O, and a pH of 7.4 in a 50 ml conical cell-trap tube or a commercially available tube. The cell-trap tube contained a constriction in a location so that approximately 15 ml of "PERCOLL" was in the lower compartment and 5 ml of "PERCOLL" was above the constriction. It was critical to completely fill the volume under the constriction with "PERCOLL" to prevent the formation of air bubbles. Generally, 20 ml of apheresed blood samples were layered on top of this gradient. The tube was centrifuged at 850×g for 30 minutes at room temperature. The cells lodged at the interface of the gradient; i.e., on top of "PERCOLL," were collected by pouring the entire content of the upper compartment of the tube into another 50 ml tube. The cell pellet in the region below the constriction were prevented from pouring off when the tube was inverted.

In order to compare the cell separation method described in the preceding paragraph with conventional methods, the test samples were also was layered on "FICOLL-HYPAQUE" (Pharmacia). The density of the stock "FICOLL" solution was at 1.077±0.001 gr/ml and the osmolality at 320 mOsm/kg H$_2$O as published by the vendor.

6.1.4. Density Adjusted Cell Sorting

Apheresed blood product was incubated with 1.4µ aminopropyl glass beads (Bangs Laboratories Inc., Carmel, Ind.) that were glutaraldehyde coated with an anti-CD45 antibody (clone ALB-12, Biodesign International, Kennebunk, Me.) for 45 minutes at room temperature. The entire blood cell mixture was layered on "PERCOLL" (1.0605±0.0005 gr/ml, 280 mOsm/Kg H$_2$O, pH 7.4) in a 50 ml tube.

6.1.5. Monoclonal Antibodies

Phycoerythrin-conjugated (PE) anti-CD34 monoclonal antibodies (hematopoietic progenitor cell marker) and fluorescein-conjugated (FITC) anti-CD45 monoclonal antibodies (pan-leukocyte marker) were obtained from Becton Dickinson, Inc. (San Jose, Calif.). Unconjugated antibodies directed to CD45, CD16 (granulocytes, monocytes), CD3 (T cells), CD14 (monocytes) were prepared in the laboratory, according to methods well known in the art.

6.1.6. Conjugation of Monoclonal Antibodies to Carrier Particles

Antibodies were conjugated to either goat anti-mouse coated magnetic beads or to goat anti-mouse coated aminopropyl glass beads by overnight incubation at room temperature. Alternatively, the antibodies could be bound directly to these beads without the goat anti-mouse bridge or could be bound via an avidin-biotin coupling reaction. In addition the antibodies could be cleaved into Fab2 fragments in order to reduce non-specific binding of cells to the beads via their Fc portion.

6.1.7. Antibody Staining and Flow Cytometric Analysis

The cells were incubated with 10 µL of an antibody and the DNA dye LDS 751 (Exciton Inc., Dayton Ohio) per $10^6$ cells for 30 min. on ice in the presence of 5% rabbit serum. Rabbit serum was used to reduce non-specific binding to the cells. The cells were washed twice with PBS and subsequently fixed with 1% paraformaldehyde. Statistical analysis was performed on $10^4$ flow events using a FACScan flow cytometry system equipped with a LYSYS II program.

6.1.8. Colony Forming (CFU) Assay/Functional Determination of Committed CD34$^+$ Cells The functional characteristics of the CD34$^+$ cells in a cell sample was determined by the colony formation assay (CFU). This assay allowed the quantification of the number of committed hematopoietic progenitor cells in the cell solution. $10^5$ cells were mixed in 2 mL semi-solid methyl cellulose containing different colony stimulating factors and erythropoietin (Terry Fox Laboratories, Vancouver). The entire mixture was incubated for 14 days at 37° C. The number of erythroid (CFU-E, BFU-E), granulocyte/macrophage (CFU-GM) and mixed (CFU-GEMM) colonies were counted under an inverted microscope (40x).

6.1.9. Long Term Culture Initiating Cell (LTC-IC) Assay/Functional Determination of Uncommitted CD34$^+$ Cells The number of uncommitted hematopoietic progenitor cells in a cell mixture was determined by the long term culture initiating culture. The cells were seeded on an irradiated stroma feeder layer and a determination of CFU's was made in function of time. Hematopoietic stem cells were able to self-renew and gave rise to CFU's in this system for a period that exceeded 5 weeks. Long term bone marrow stromal cultures were initiated in 96 well plates ($10^6$ cells in 200 µl per well) in α-MEM medium supplemented with 12.5% horse serum, 12.5% fetal calf serum, 2 mM L-glutamine, 0.2 mM i-inositol, 20 µM folic acid, $10^{-4}$M 2-mercaptoethanol and were kept at 33° C. in a humidified atmosphere. At weekly intervals, half the medium was removed and replaced by an equal volume of fresh medium. After 2 weeks of culture, the confluent stroma layers were gamma irradiated (2000 rad) to kill endogenous hematopoietic cells. Unfractionated samples and cell preparations after separation were seeded onto the irradiated stroma layers in the same medium supplemented with $10^{-6}$M hydrocortisone. After five weeks of culture the adherent and non-adherent cells were collected and screened in the CFU assay as in Section 6.1.8, infra.

6.1.10. Natural Killer (NK) Cell Assay

K562 target cells were labeled with 100 µCi $^{51}$Cr for 1 hour at 37° C. and then washed four times and counted. The target cells were co-cultured for 4 hours in V-bottom 96 well multiwell plates with unfractionated apheresed blood and cells from the different fractions after cell separation. Effector and target cells were mixed at different ratios, 100:1, 50:1, 25:1 and 12:1. For example, the 100:1 ratio contained $5\times10^5$ effector cells and $5\times10^3$ target cells. After the incubation period, 100 μl of the supernatant was harvested and counted in a scintillation counter. Maximal and spontaneous $^{51}$Cr release was measured counting either 50 μl of the stock target solution and supernatant from the effectors by themselves, respectively. The percent cytotoxicity was determined according to formula:

$$\text{Percent Cytotoxicity} = \frac{\text{cpm experiment} - \text{cpm spontaneous release}}{\text{cpm maximal release} - \text{cpm spontaneous release}}$$

6.1.11. Mixed Lymphocyte Culture and Natural Suppressor Cell Activity

Cells from two different buffy coats were mixed in a flat bottom 96 well multiwell plate at $10^5$ cells of each. One of the buffy coats received 3000 rad and was referred to as the "stimulators". The other buffy coat was used untreated and referred to as "responders." Unfractionated apheresed peripheral blood products (APBL) or cells from the different density fractions were added to these co-cultures at $10^5$ cells per well. These cells were referred to as "suppressors" and received 1500 rad prior to being added to the MLR. The cells were cultured for 5 days and then pulsed with [$^3$H]-thymidine (1 μCi/well). 18 hours later, the cells were harvested and the amount of thymidine incorporated determined in a scintillation counter. The percent suppression induced by the suppressor cells was determined by the formula:

$$\text{Percent Suppression} = \frac{\text{cpm control} - \text{cpm experiment}}{\text{cpm experiment}}$$

6.2. EXAMPLES

6.2.1. Enrichment of Hematopoietic Stem Cells from Blood

Table 1 presents results from an experiment in which "PERCOLL" was used as the density gradient material. "PERCOLL" was prepared and adjusted to physiologic osmolality of 280±10 mOsm/kg $H_2O$ and physiologic pH of 7.4. For this study, the starting cell mixture was a sample of apheresed blood from a non-Hodgkin lymphoma patient who had been treated with G-CSF. When the gradient was adjusted to different densities, the results showed that when the density was at 1.0600 gr/ml or above, there was an about 60–90% increase of CD34$^+$ cells in the interface fraction over the gradients adjusted to lower densities. Furthermore, the percentage of total cell yield also increased slightly at 1.0600 gr/ml or above. Thus, in order to recover a high percentage of total CD34$^+$ cells from the starting cell mixture, the density of 1.0605 gr/ml was chosen. It was further determined that an accuracy of within ±0.0005 gr/ml was preferable to ensure high yield enrichment of CD34$^+$ cells.

TABLE 1

| Density "PERCOLL" (gr/ml) | | Percentage of Total Cell Yield | Percentage of CD34$^+$ Cell Yield |
|---|---|---|---|
| Unfractionated | | 100% | 100% |
| 1.0590 | Interface | 11% | 32% |
| | Pellet | 85% | 68% |

TABLE 1-continued

| Density "PERCOLL" (gr/ml) | | Percentage of Total Cell Yield | Percentage of CD34$^+$ Cell Yield |
|---|---|---|---|
| 1.0595 | I | 18% | 45% |
| | P | 78% | 55% |
| 1.0600 | I | 26% | 80% |
| | P | 70% | 20% |
| 1.0605 | I | 31% | 83% |
| | P | 63% | 17% |
| 1.0610 | I | 35% | 89% |
| | P | 60% | 11% |

Additionally, "PERCOLL" was adjusted to a density of 1.0605 gr/ml and osmolality of 280 mOsm/kg $H_2O$, and compared with stock "FICOLL" which had a density of 1.077±0.001 gr/ml and 320 mOsm/kg $H_2O$. Table 2 shows that when the gravitational force of centrifugation increased, more CD34$^+$ cells were pelleted in the stock "FICOLL" gradient. Since the use of unadjusted "FICOLL" was the standard material used for density gradient separation of CD34$^+$ cells from a cell mixture, these results show that a precisely defined density range could substantially enhance the high yield enrichment of CD34$^+$ cells from a cell mixture. As shown in Table 2, the percentage of CD34$^+$ cell yield after centrifugation at 1500× g increased about 2 fold over that achieved by a conventional method.

TABLE 2

| | "FICOLL" | | "PERCOLL" | |
|---|---|---|---|---|
| Gravitational Force (xg) | Percentage of CD34$^+$ Cell Purity | Percentage of CD34$^+$ Cell Yield | Percentage of CD34$^+$ Cell Purity | Percentage of CD34$^+$ Cell Yield |
| 200 | 0.62% | 1% (Baseline) | 0.83% | 0.64% |
| 350 | 0.63% | 1.07% | 0.85% | 0.49% |
| 800 | 0.74% | 0.6% | 1.92% | 0.88% |
| 1500 | 0.62% | 0.48% | 2.05% | 0.83% |

Absolute cell numbers and cell recovery were determined using apheresed blood samples from non-Hodgkin lymphoma patients. The mean cell recovery from 5 samples was variable but was always in the range of 90%. Since cell counting was performed after a washing step, that may account for cell loss up to 10%. CD34$^+$ cell recovery was determined from the 5 different blood samples, and was always in the range of 90%. This result was similar to the non-specific cell loss shown above, thus it was not due to a specific depletion of the total number of CD34$^+$ cells or a change in the CD34 expression by hematopoietic progenitor cells. When the quantitative recovery of CFU's was determined, the recovery of CFU was also in the range of 90%. Therefore, the cell separation procedure by the 1.0605 gr/ml density gradient did not change the functional potential of hematopoietic progenitor cells to form colonies.

In addition, the quantitative distribution of the CFU over the gradient was determined. The results in FIG. 12 show that only minor numbers of CFU were observed in the pellet fractions and approximately 90–100% of the CFU were present in the interface of 1.0605 gr/ml "PERCOLL". This result directly correlated with the quantitative distribution of CD34$^+$ cells on the gradient as shown in Table 1. Also, it was observed that 100% of the CFU-GEMM were present in the interface (FIG. 13). LTC-IC assays showed that between 90–100% of the uncommitted hematopoietic stem cells were present in the interface (FIG. 14).

Hence, these data demonstrate that the centrifugation of apheresed blood on a single-layer gradient adjusted to 1.0605± 0.0005 gr/ml resulted in a minor non-specific loss (10% or less) of the total cell product. However, while the interface represented approximately 30% of the total cell number, this cell population contained 70–90% of the CD34+ cells and more than 90% of the CFU's. The interface contained 100% of the CFU-GEMM, and since CFU-GEMM represented progenitor cells with a low degree of hematopoietic commitment and a limited degree of self renewal, the interface also contained the uncommitted hematopoietic stem cells. The results obtained with the LTC-IC assays further support this conclusion. This simplified procedure may allow the automation of CD34+ cell enrichment in a completely closed system. Furthermore, experiments performed in cell-trap tubes produced similar results with an even greater degree of consistency.

6.2.2. Additional Biological Features of Density Separated BM and APBL Products

Graft versus host disease (GvHD) is induced by the T-cells that are present in the donor allografts. Consequently, some transplant protocols included the total removal of T-cells from the graft prior to transplantation. Although these methods successfully reduced GvHD, they also resulted in increased incidence of graft failure and tumor relapse. In other words, the presence of a limited number of T-cells may be beneficial for the survival chances of allotransplant patients. In this context, a "PERCOLL" gradient was adjusted to a density of 1.0605±0.0005 gr/ml to test for its ability to remove T-cells. Normal bone marrow and apheresed blood samples from G-CSF treated normal individuals were processed on the density gradient. The cells from the interface and pellet fractions were stained with the T-cell specific anti-CD3 antibodies. FIG. 15 shows that for both tissue sources the interface contained between 10% and 20% of the total number of T-cells that were present in the unprocessed material.

In vitro studies showed that human bone marrow contained low density cells which blocked in vitro alloresponses in the mixed lymphocyte reactions (MLR). Based on the fact that this suppressive activity was HLA non-restricted, it was referred to in the literature as natural suppressor (NS) activity. A "PERCOLL" density gradient was adjusted to a density of 1.0605±0.0005 gr/ml to test for its ability to enrich cells with NS activity. Apheresed blood samples from lymphoma patients and from normal individuals that received G-CSF treatment were centrifuged on a discontinuous five layer gradient, and the interfaces and pellet were screened for their potential to suppress the mixed lymphocyte culture. FIG. 16 shows that cells with NS activity had a density equal or lighter than 1.0605 gr/ml. Consequently, more than 90% of the NS activity was present in the final cell preparation after centrifugation on a 1.0605 gr/ml gradient.

NK cells had been shown to kill autologous tumor cells. From a clinical perspective, it may be beneficial to have increased numbers of NK cells in the transplant to reduce tumor relapse. In this context, the density of the NK cells was determined on a discontinuous five-layer "PERCOLL" gradient. NK cells also showed a density equal to or lighter than 1.0605 gr/ml. Consequently, more than 90% of NK cells was present in the final cell preparation after centrifugation on a 1.0605 gr/ml gradient, as shown in FIG. 17.

6.2.3. Enrichment of CD34+ Cells Using Density Adjusted Cell Sorting

FIG. 18 shows the result of a representative experiment in which CD34+ cells were enriched by removing CD34− cells with an anti-CD45 mAb coupled to a heavy carrier (such as magnetic beads or aminopropyl glass beads). In this particular experiment the total cell number was reduced 82% and the CD34 yield was around 40%. The CD34 purity increased from 2% to approximately 20%. Since the anti-CD45 antibody removed also some of the CD34+ cells, this method could improved by using a mixture of other antibodies to deplete non-stem cells.

7. EXAMPLE

Method for Binding Antibody to Glass Beads 7.1 Preparation of the Beads

Silica beads (1.4 microns) obtained from Bangs Laboratories, Carmel, Ind. were washed with concentrated HCl for 2 hours at room temperature and vortexed intensely every 15 minutes to brake up bead clumps. After washing, the beads were centrifuged at 850 g for 5 minutes. The HCL containing supernatant was decanted and the beads were washed with deionized $H_2O$ with intensive vortexing to brake up the clumps.

The beads were incubated at room temperature overnight in concentrated nitric acid with constant stirring using a magnetic stirrer. The beads were then centrifuged at 850 g for 5 minutes and washed 3 times with deionized water, using 50 ml of deionized $H_2O$ at each step. The beads were vortexed intensely in between each wash to avoid bead clumping. To prevent microbacterial contamination, the beads were stored at 0–4 degrees centigrade in deionized $H_2O$ until further use.

7.2 Silanization of the Beads

To silanize the beads, either 3-aminopropyltriethoxysilane, (3-iodopropyl)trimethoxysilane or [1-9trimethoxysilyl)-2(m-(or p) chloromethyl)phenyl] ethane were used. Forty mls of silane solution (a 10% solution in 95% ethanol/deionized $H_2O$) was added per 4 gr of beads. The bead mixture was rotated end over end for 1 hour at room temperature. The beads were centrifuged at 850 g for 5 minutes and the excess silane was washed off using 95% ethanol/deionized $H_2O$ in a volume of 100 ml. The beads were vortexed intensely in between each wash step to avoid bead clumping. After the washing step, the beads can be dried and stored. Alternatively the beads can be stored in 95% ethanol/deionized $H_2O$ in the cold which prevents clumping of the beads.

7.3 Antibody Coupling to the Aminopropyl Glass

The silanized beads were incubated overnight in 2.5% glutaraldehyde at room temperature. The next day, the beads were centrifuged at 850 g for 5 minutes and the free glutaraldehyde was washed off with deionized $H_2O$ in a volume of 100 ml per 5 gr beads. The beads were vortexed intensely in between each wash step to avoid bead clumping.

The antibody was added to the aminopropyl beads in an excess, at least 3 mg/m² total bead surface and rotated end over end overnight at room temperature. The next day, the beads were centrifuged at 850 g for 5 minutes and the free protein was washed off with 100 ml of deionized $H_2O$. The beads were vortexed intensely in between each wash step to avoid bead clumping. The beads were stored in deionized $H_2O$ containing 0.1 sodium azide in the cold. The final bead suspension should contain 70–90% single beads and 10–30% predominantly duplet and triplet beads.

The binding efficiency of the antibody conjugated beads (in terms of the percent of beads that are coated) can be determined using flow cytometric analysis and a fluorescinated antibody directed to the coupled antibody. Alternatively, the antibody may be added to the silanized beads directly without the glutaraldehyde linking.

The present invention is not to be limited in scope by the exemplified embodiments, which are intended as illustrations of individual aspects of the invention. Indeed, various modifications for the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A method of enriching $CD34^+$ cells from a cell mixture, comprising:

layering a cell mixture containing $CD34^+$ cells into a centrifuge tube, said tube having a first closed end defining an inner bottom wall and an opposite open end, an annular member disposed in said tube and defining an opening therethrough, wherein said opening has an area less than the area of a cross section of said tube, said annular member defining a lower portion of the tube extending between said member and said tube bottom wall and an upper portion above said annular member, said tube containing a density gradient solution which fills said lower portion and a part of said upper portion, said density gradient solution having an osmolality of 280±10 mOsm/kg $H_2O$ and a specific density within 0.0005 gr/ml of the specific density of said $CD34^+$ cells;

centrifuging said tube at a gravitational force sufficient to pellet cells having specific densities greater than the specific density of the density gradient material in said tube; and collecting from the upper portion of said tube an enriched population of $CD34^+$ cells.

2. The method of claim 1 wherein the specific density of the density gradient material is within 0.0002 gr/ml of the specific density of said $CD34^+$ cells.

3. The method of claim 2 wherein the specific density of the density gradient material is 1.0605 gr/ml.

4. The method of claim 3 wherein the $CD34^+$ cells are colony forming cells.

5. The method of claim 3 wherein the $CD34^+$ cells are cells with long term culture initiating capability.

6. The method of claim 1 wherein the $CD34^+$ cells in the upper portion are collected by decantation.

7. The method of claim 1 further comprising incubating said cell mixture with a cell type-specific binding agent linked to carrier particles prior to centrifugation, said particles having a specific density that is at least 0.001 gr/ml greater than the specific density of said density gradient solution.

8. The method of claim 7 wherein the cell-type specific binding agent specifically binds to non-CD $34^+$ cells.

9. The method of claim 8 wherein the agent is an antibody.

10. The method of claim 9 wherein the antibody is directed to CD45 antigen.

11. The method of claim 7 wherein the particles are silica beads.

12. The method of claim 11 wherein the beads are silane activated.

13. The method of claim 12 wherein the silane is 3-amino propyltriethoxy silane.

14. A method of enriching $CD34^+$ cells from a cell mixture, comprising:

layering a cell mixture containing fetal cells into a centrifuge tube, said tube containing a density gradient solution having an osmolality of 280±10 mOsm/kg $H_2O$ and a specific density of 1.0605±0.0005 gr/ml;

centrifuging said tube at a gravitational force sufficient to pellet cells having specific densities greater than 1.0610 gr/ml; and collecting an enriched population of $CD34^+$ cells from an interface above the density gradient solution.

15. The method of claim 14 wherein the $CD34^+$ cells are colony forming cells.

16. The method of claim 14 wherein the $CD34^+$ cells are cells with long term culture initiating capability.

17. The method of claim 14 further comprising incubating said cell mixture with a cell type-specific binding agent linked to carrier particles prior to centrifugation, said particles having a specific density that is at least 0.001 gr/ml greater than 1.0605 gr/ml.

18. The method of claim 17 wherein the cell type-specific binding agent specifically binds to non-CD $34^+$ cells.

19. The method of claim 18 wherein the agent is an antibody.

20. The method of claim 19 wherein the antibody is directed to CD45 antigen.

21. The method of claim 17 wherein the particles are silica beads.

22. The method of claim 21 wherein the beads are silane activated.

23. The method of claim 22 wherein the silane is 3-amino propyltriethoxy silane.

24. The method of claim 1 wherein the density gradient solution is selected from the group consisting of "PERCOLL", "FICOLL", "FICOLL-HYPAQUE", albumin, sucrose and dextran.

25. The method of claim 14 wherein the density gradient solution is selected from the group consisting of "PERCOLL", "FICOLL", "FICOLL-HYPAQUE", albumin, sucrose and dextran.

26. A centrifugation tube, comprising:

a tube adapted for centrifugation having a first closed end defining an inner bottom wall and an opposite open end;

an annular member disposed in said tube and defining an opening therethrough, wherein said opening has an area less than the area of a cross section of said tube, said annular member defining a lower portion of the tube extending between said member and the tube bottom wall and an upper portion above said annular member; and a density gradient solution having a density of 1.0605±0.0005 gr/ml, and filling said lower portion and a part of said upper portion.

27. The tube of claim 26, wherein said density gradient solution fills the upper portion to a level at least about 1 mm above said annular member.

28. The tube of claim 26, wherein said annular member is formed integrally with said tube.

29. The tube of claim 26, wherein said annular member is slideably disposed within said tube to permit adjustment of the volume of the lower portion.

30. The tube of claim 26 wherein said annular member defines a plurality of openings.

31. A centrifuge syringe comprising:

a generally cylindrical container adapted for centrifugation, having an inner wall, a first end and a second end, said first end and second end each defining central orifices;

a hollow needle secured to the first end by a detachable connection and communicating with said first end orifice;

a plunger adapted to be slideably positioned within said container, said plunger comprising a cylindrical housing having a bottom wall and a top wall defining therebetween a fluid receiving space, said top wall formed by an annular member defining an opening;

a circumferential seal around said cylindrical housing cooperating with said container inner wall to substantially prevent fluid passage therebetween;

a handle removably connected to said plunger and adapted to move longitudinally through the central orifice of the second end of said container; and density gradient material having a density of 1.0605±0.0005 gr/ml disposed within said fluid receiving space and extending above said annular member.

32. A method of extracting and centrifuging a fluid specimen utilizing a syringe including an outer container with an inner plunger having a bottom wall joined to a top wall defining therebetween a fluid space, said top wall formed by an annular member having an opening, and said bottom wall connected to a handle, comprising the steps of:

filling said fluid space and syringe with a density gradient material having a density of 1.0605±0.0005 gr/ml to a level above said top wall;

drawing a sample into the container and on top of the density gradient material by pulling said handle;

removing the handle from the plunger;

placing the syringe in a centrifuge;

applying centrifugal force to said syringe; and removing at least a portion of said sample remaining above the annular member after applying centrifugal force.

* * * * *

UNITED STATES PATENT AND TRADEMARK OFFICE
CERTIFICATE OF CORRECTION

PATENT NO. : 5,474,687
DATED : December 12, 1995
INVENTOR(S) : Peter Van Vlasselaer It is certified that error appears in the above-indentified patent and that said Letters Patent is hereby corrected as shown below:

Column 8, line 64, after the word "syringe", delete "10" and insert --110--.

Column 8, line 66, delete "10" and insert --110--; after the word "container", delete "14" and insert --114--.

Column 8, line 67, delete "12" and insert --112--; delete "13" and insert --113--.

Column 9, line 1, after the word "handle", delete "16" and insert --116--; after the word "plunger", delete "18" and insert --118--; and after the word "Fitting", delete 12 and insert --112--.

Column 9, line 3, after the word "fitting", delete "12" and insert --112--.

Column 9, line 8, after the word "Handle", delete "16" and insert --116--; and after the word "knob", delete "22" and insert --122--.

Column 9, line 9, after the word "connection", delete "24" and insert --124--, and after the word "plunger", delete "18" and insert --118--.

Column 9, line 10, after the word "plunger", delete "18" and insert --118--.

Column 9, line 13, after the word "wall", delete "26" and insert --126--.

Column 9, line 14, after the word "connection", delete "24" and insert --124--; and after the word "wall" and delete "27" and insert --127--.

Column 9, line 17, after the word "member", delete "28" and insert --128--.

Column 9, line 18, after the word "opening", delete "29" and insert --129--; and after the word "wall", delete "27" and insert --127--.

Column 9, line 20, after the word "wall", delete "27" and insert --127--; and after the word "container", delete "14" and insert --114--.

Column 9, line 21, after the word "connection", delete "24" and insert --124--.

Column 9, line 23, delete "24" and insert --124--; and after the word "handle", delete "16" and insert --116--.

Column 9, line 24, after the word "connector", delete "24" and insert --124--.

Column 9, line 25, after the word "handle", delete "16" and insert --116--.

Column 9, line 27, after the word "plunger", delete "18" and insert --118--; and after the word "material", delete "20" and insert --120--.

UNITED STATES PATENT AND TRADEMARK OFFICE
CERTIFICATE OF CORRECTION

PATENT NO. : 5,474,687
DATED : December 12, 1995
INVENTOR(S) : Peter Van Vlasselaer It is certified that error appears in the above-indentified patent and that said Letters Patent is hereby corrected as shown below:

Column 9, line 30, after the word "opening", delete "29" and insert --129--.

Column 9, line 34, after the word "member", delete "28" and insert --128--.

Column 9, line 36, after the word "member", delete "28" and insert --128--.

Column 9, line 38, after the word "syringe", delete "10" and insert --110--, and after the word "specimen", delete "30" and insert --130--.

Column 9, line 39, after the word "needle", delete "13" and insert --113--; and after the word "fitting", delete "12" and insert --112--.

Column 9, line 40, after the word "handle", delete "16" and insert --116--; and after the word "plunger", delete "18" and insert --118--.

Column 9, line 41, after the word "container", delete "14" and insert --114--.

Column 9, line 42, after the word "fitting", delete "12" and insert --112--.

Column 9, line 51, after the word "specimen", delete "30" and insert --130--.

Column 9, line 52, after the word "container", delete "14" and insert --114--.

Column 9, line 54, after the word "material", delete "20" and insert --120--.

Column 9, line 55, after the word "needle", delete "13" and insert --113--.

Column 9, line 68, after the word "container", delete "14" and insert --114--; and after the word "handle", delete "16" and insert --116--.

Column 10, line 1, after the word "connection", delete "24" and insert --124--.

Column 10, line 2, after the word "container", delete "14" and insert --114--; and after the word "handle", delete "16" and insert --116--.

Column 10, line 6, after the word "handle", delete "16" and insert --116--; and after the word "plunger", delete "18" and insert --118--.

UNITED STATES PATENT AND TRADEMARK OFFICE
CERTIFICATE OF CORRECTION

PATENT NO. : 5,474,687
DATED : December 12, 1995
INVENTOR(S) : Peter Van Vlasselaer It is certified that error appears in the above-identified patent and that said Letters Patent is hereby corrected as shown below:

Column 10, line 7, after the word "container", delete "14" and insert --114--.

Column 10, line 8, after the word "container", delete "14" and insert --114--; and after the word "pellet", delete "32" and insert --132--.

Column 10, line 10, delete "18" and insert --118--; after the word "material", delete "20" and insert --120--; and after the word "pellet", delete "32" and insert --132--.

Column 10, line 11, after the word "portion", delete "34" and insert --134--.

Column 10, line 12, after the word "diluent", delete "33" and insert --133--.

Column 10, line 13, after the word "material", delete "20" and insert --120--; and after the word "member", delete "28" and insert --128--.

Column 10, line 14, after the word "portion", delete "34" and insert --134--.

Column 10, line 15, after the word "syringe", delete "10" and insert --110--.

Column 10, line 16, after the word "arrow", delete "37" and insert --137--.

Column 10, line 17, after the word "material", delete "20" and insert --120--; and after the word "pellet", delete "32" and insert --132--.

UNITED STATES PATENT AND TRADEMARK OFFICE
CERTIFICATE OF CORRECTION

PATENT NO. : 5,474,687
DATED : December 12, 1995
INVENTOR(S) : Peter Van Vlasselaer It is certified that error appears in the above-identified patent and that said Letters Patent is hereby corrected as shown below:

Column 10, line 18, after the word "handle", delete "16" and insert --116--; and after the word "plunger", delete "18" and insert --118--.

Column 10, line 19, delete "24" and insert --124--.

claim 14, at Column 19, line 66, after the word "containing", please delete the term "fetal" and in its place insert the term --$CD34^+$--.

Signed and Sealed this

Twelfth Day of May, 1998

*Attest:*

BRUCE LEHMAN

*Attesting Officer*        *Commissioner of Patents and Trademarks*